US005491220A

United States Patent [19]

Seddon et al.

[11] Patent Number: 5,491,220

[45] Date of Patent: Feb. 13, 1996

[54] SURFACE LOOP STRUCTURAL ANALOGUES OF FIBROBLAST GROWTH FACTORS

[75] Inventors: Andrew P. Seddon, Monroe; Luyuan Li, New City; Peter Böhlen, Peekskill, all of N.Y.; Magdalena Eisinger, Demarest, N.J.; Avner Yayon, Moshav Sitra, Israel

[73] Assignees: Yeda Research and Development Co., Ltd., Rehovat, Israel; American Cyanamid Company, Wayne, N.J.

[21] Appl. No.: 290,373

[22] Filed: Aug. 15, 1994

Related U.S. Application Data

[63] Continuation-in-part of Ser. No. 126,973, Sep. 24, 1993, abandoned.

[51] Int. Cl.$^6$ .......................... C07K 14/50; C12N 15/18

[52] U.S. Cl. .......................................... 530/399; 530/350

[58] Field of Search .................................... 530/350, 399

[56] References Cited

U.S. PATENT DOCUMENTS 4,378,347 3/1983 Franco .................................... 424/108

OTHER PUBLICATIONS

Imamura, T. et al., J. Cell. Biochem. Suppl. 18 Part A: 317, 1994.

Imamura, T. et al., *Biochimica et Biophysica Acta*, 1266(2):124–130, 1995.

Friedman, S. et al., *FASEB J.*, 8(7):A1461, 1994.

Baird, A., et al., Proc. Nat. Acad. Sci. USA 85: 2324–2328 (1988).

Baird, A., and Bohlen, P., *Handbook of Exp. Pharmacol.* 95(1): 369–418, Springer, 1990.

Davidson, J. M., et al., J. Cell Bio. 100: 1219–1227 (1985).

Eriksson, E. A., et al., Proc. Nat. Acad. Sci. USA 88: 3441–3445 (1991).

Feige, J. J. et al., Proc. Nat. Acad. Sci. USA 86: 3174–3178 (1989).

Givol, D., and Yayon, A., FASEB J. 6: 3362–3369 (1992).

Gospardarowicz, D., et al *Proc. Nat. Acad. Sci.* 81: 6963–6967 (1984).

Howden, G. F., and Silver, I. A., *Int. Endodontic J.* 13: 3–6 (1980).

Hynes, T. R., et al, *Nature* 339: 73–76 (1989).

Jaye, M., et al., *Biochim. Biophys. Acta* 1135: 185–199 (1992).

Johnson, D. E., and Williams, L. T., *Adv. Can. Res.* 60: 1–41 (1993).

Miyamoto, M. et al. *Mol Cell. Biol.* 13: 4251–4259 (1993).

Moscatelli, D., *J. Cell. Physiol.* 131: 123–130 (1987).

Presta, M., et al., B.B.R.C. 185: 1098–1107 (1992).

Seddon, A. P. et al, *Annals N.Y. Acad. Sci.* 638: 98–108 (1991).

Seno, M., et al., *Eur. J. Biochem* 188; 239–245 (1990).

Tanaka, A., et al. *Proc. Natl. Acad. Sci. USA* 89: 8928–8932 (1992).

Werner, S., et al., *Mol. Cell. Bio.* 12:82–88 (1992).

Yayon, A., et al., *EMBO J.* 11: 1885–1890 (1992).

Zhang, J., et al., *Proc. Nat. Acad. Sci. USA* 88: 3446–3450 (1991).

Zhu, H., et al., *Science* 251: 90–93 (1991).

*Primary Examiner*—Marianne P. Allen

*Attorney, Agent, or Firm*—St. Onge Steward Johnston & Reens

[57] ABSTRACT

Structural analogues of fibroblast growth factors have an amino acid sequence replacement in the ninth or tenth β-strand of the factor, or the sequence that corresponds to the surface loop that connects the ninth and tenth β-strands, such that the folding of the molecule is not significantly perturbed. Preferred analogues have the amino acid sequence replacement in the surface loop that extends from the ninth β-strand to the tenth β-strand and have the overall secondary and tertiary structure of the original factor, and bind to heparin and a member or members of the fibroblast growth factor receptor family with high affinity. In some embodiments, the analogues are prepared by replacing the surface loop sequence that connects the ninth and tenth β-strand with another amino acid sequence such as a loop sequence from another structurally related fibroblast growth factor or an interleukin. Preferred analogues exhibit different biological properties and/or receptor binding specificity profiles from native factors.

9 Claims, 10 Drawing Sheets

```
FGF-2    Asn Asn Tyr Asn Thr Tyr Arg Ser Arg Lys Tyr         Thr Ser Trp Tyr Val Ala Leu Lys
                                                           (Ser)
          110             115              120                        125

FGF-1    Asn His Tyr Asn Thr Tyr Ile Ser Lys Lys His Ala Glu Lys Asn Trp Phe Val Gly Leu Lys
                                                               (His)

IL-Iß    Asn Asn Lys Leu Glu Phe Glu Ser Ala Gln Phe         Pro Asn Trp Tyr Ile Ser Thr Ser
```

Figure 1

| | β-strand 9 | LOOP (120) | β-strand 10 (125) |
|---|---|---|---|
| FGF-1 | NTYIS | KKHAEKN-------------- | WFVGLK |
| FGF-2 | NTYRS | RKYTS---------------- | WYVALK |
| FGF-3 | NTYAS | RLYRTVSSTPGARRQPSAERL | WYVSVN |
| FGF-4 | NAYES | YKYPG---------------- | MFIALS |
| FGF-5 | NTYAS | AIHRTEKTGRE---------- | WYVALN |
| FGF-6 | NAYES | DLYQG---------------- | TYIALS |
| FGF-7 | NTYAS | AKWTHNGGE------------ | MFVALN |
| FGF-8 | TALQN | AKYEG---------------- | WYMAFT |
| FGF-9 | NTYSS | NLYKHVDTGRR---------- | YYVALN |
| | * * * | | ** * |

Figure 7

SURFACE LOOP STRUCTURAL ANALOGUES OF FIBROBLAST GROWTH FACTORS

RELATED U.S. APPLICATION DATA

This is a continuation-in-part of U.S. patent application Ser. No. 08/126,973, filed Sep. 24, 1993, now abandoned.

TECHNICAL FIELD OF THE INVENTION

This invention relates to fibroblast growth factor analogues having different primary structures in a surface loop that connects the ninth and tenth β-strands. The analogues retain overall secondary and tertiary protein structural similarities to the original factors but exhibit different biological properties and receptor binding specificity profiles.

BACKGROUND OF THE INVENTION

Polypeptide growth factors are hormone-like modulators of cell proliferation and differentiation. Growth factors are responsible for the regulation of a variety of physiological processes, including development, regeneration, and wound repair, and have been associated with normal as well as with pathophysiological processes. Numerous growth factors have been identified in various tissues and cells, and names that have been applied to these factors include epidermal growth factor, platelet-derived growth factor, nerve growth factor, hematopoietic growth factors, and fibroblast growth factor.

Fibroblast growth factor (FGF) was first described as an activity derived from bovine brain or pituitary tissue which was mitogenic for fibroblasts and endothelial cells. It was later noted that the primary mitogen from brain was different from that isolated from pituitary. These two factors were named acidic and basic FGF, respectively, because they had similar biological activities but differed in their isoelectric points. Acidic and basic FGF are proteins containing approximately 154 amino acids. Their amino acid sequences are related, with approximately 55% sequence identity between them.

Acidic and basic fibroblast growth factors are now known to be members of a larger family of heparin-binding growth factors that collectively trigger a variety of biological responses in many cell types, including those of mesoderm and neuroectoderm origin, such as endothelial cells, smooth muscle cells, adrenal cortex cells, prostatic and retina epithelial cells, oligodendrocytes, astrocytes, chrondocytes, myoblasts, and osteoblasts. As original family members, acidic and basic FGF are now denoted FGF-1 and FGF-2, respectively. Seven other members of the family have been identified on the basis of their modulation of cell proliferation and differentiation, and their sequence homology to other FGFs.

In addition to eliciting a mitogenic response that stimulates cell growth, fibroblast growth factors can stimulate a large number of cell types to respond in a non-mitogenic manner. These activities include promotion of cell migration into wound areas (chemotaxis), initiation of new blood vessel formulation (angiogenesis), modulation of nerve regeneration and survival (neurotrophism), modulation of endocrine functions, and stimulation or suppression of specific cellular protein expression, extracellular matrix production and cell survival (Baird, A., and Böhlen, P., *Handbook of Exp. Pharmacol.* 95(1): 369–418, Springer, 1990).

These properties provide a basis for using fibroblast growth factors in therapeutic approaches to accelerate wound healing, nerve repair, collateral blood vessel formation, and the like. For example, fibroblast growth factors have been suggested to minimize myocardium damage in heart disease and surgery (U.S. Pat. No. 4,378,347 to Franco).

Current research regarding FGF-2 and other FGFs has centered on the molecular details of the receptor-mediated pathways by which their diverse physiological activities are expressed, as a way to gain information for the design of therapeutically useful agents that can either mimic or inhibit the action of these factors. Since the primary structure of FGF-2 isolated from a variety of sources is known, and bovine and human FGF-2 have been cloned and expressed in *E. coli* and *S. cervisiae,* recent attention has focused on secondary and tertiary structure.

The 3-dimensional structures of FGF-1 and FGF-2 have been determined (Eriksson, E. A., et al., *Proc. Nat. Acad. Sci. U.S.A.* 88: 3441–3445 (1991), Zhang, J., et al., *Proc. Nat. Acad. Sci. U.S.A.* 88: 3446–3450 (1991), and Zhu, H., et al., *Science* 251: 90–93 (1991)). In these studies, FGF-1 and FGF-2 were shown to exhibit a folding pattern strikingly similar to that observed for the cytokine interleukin-1α, and interleukin-1β (IL-1α and IL-1β), protein factors produced by macrophages and T-cells in response to antigenic or mitogenic stimulation, though the primary structures of interleukin-1 polypeptides have only about a 10% amino acid sequence correspondence to FGFs.

The overall structure of FGF-2 can be described as a trigonal pyramid where each of the three sides are built of two β-strands together forming a β-sheet barrel of six antiparallel strands (Eriksson, E. A., et al., *Proc. Nat. Acad. Sci. U.S.A.* 88: 3441–3445 (1991)). The base of the pyramid is built of six additional β-strands extending from the three sides of the pyramid to close one end of the barrel for a total of twelve β-strands. Thus, a threefold repeat is observed in the folding of the polypeptide chain and a pseudo-three-fold axis passes through the center of the base of the molecule and extends through the apex of the pyramid (ibid.). Of the amino acids conserved within the FGF family of proteins, most are located within the core β-strand regions of FGF-2, supporting the expectation that each of these proteins has an overall 3-dimensional structure similar to that of FGF-2.

The biological responses of FGF are mediated by the heparan sulfate-dependent binding of the growth factor to specific cell surface receptors (Givol, D., and Yayon, A., *FASEB J.* 6: 3362–3369 (1992) and Jaye, M., et al., *Biochim. Biophys. Acta* 1135: 185–199 (1992)), yet the molecular interactions of heparin and receptor with FGF and the exact nature of the events of the signal transduction pathway are unknown. Studies employing synthetic peptides related to the FGF sequence showed that FGF-2 (33–77) and (106–129) bind to heparin and act as weak partial agonists and antagonists in a mitogenic assay of FGF activity (Baird, A., et al. *Proc. Nat. Acad. Sci. U.S.A.* 85: 2324–2328 (1988)). The same study identified a sequence, FGF-2 (115–124), involved in receptor binding. The segment begins in the middle of the ninth β-strand, makes a somewhat open loop on the surface of the folded molecule, and terminates at the beginning of the tenth β-strand. This sequence (118–122) in the native protein forms a small surface loop that is close to a cluster of basic surface residues that may form a putative heparin binding site (Zhang, J., et al., *Proc. Nat. Acad. Sci. U.S.A.* 88: 3446–3450 (1991)).

This sequence also contains Thr-121, which can be phosphorylated by a cAMP-dependent protein kinase (Feige, J.

J., and Baird, A., *Proc. Nat. Acad. Sci. U.S.A.* 86: 3174–3178 (1989)); Thr-121 is denoted in the paper as Thr-112 since the investigators employed the N-terminally truncated form of the polypeptide, which exhibits full biologic activity but has 146 rather than the usual 154 amino acids). Phosphorylation of Thr-121 results in the generation of a form of the protein that exhibits an increased capacity to compete with radiolabelled FGF-2 binding to its receptor, but no difference in the biological properties of the phosphorylated and non-phosphorylated forms of the protein were observed (ibid.). In contrast to FGF-2, FGF-1 is not a substrate for the kinase. The data are consistent with the hypothesis that the sequence 115–124 is involved in receptor binding, but they do not define the complete receptor binding domain of the molecule, nor do they demonstrate the physiological significance of phosphorylation of Thr-121.

In addition to heparin and receptor binding regions, there is evidence that specific sequences in FGF influence ligand-induced signal transduction. For example, deletion of residues 27–32 of FGF-2 (Lys-Asp-Pro-Arg-Leu) or mutation of the basic residues Arg-118, Lys-119, Lys- 128, and Arg-129 did not appear to affect the mitogenic activity of the protein, but eliminated activation of plasminogen activator gene expression (Eur. Pat. Ap. Pub. No. 363,675 to Bergonzoni, L., et al., and Presta, M., et al., *Biochem. Biophys. Res. Com.* 185: 1098–1107 (1992)).

At least four different fibroblast growth factor receptors (FGFR) have been identified (Werner, S., et al., *Mol. Cell. Bio.* 12: 82–88 (1992)), and functional differences between different receptor forms have been observed. Different FGF receptor forms derived from the same gene via alternative splicing have different ligand binding properties, and analogous splice variants from different FGF receptor genes bind different members of the FGF family (Johnson, D. E., and Williams, L. T., *Adv. Can. Res.* 60: 1–41 (1993)). Thus, fibroblast growth factor receptors exhibit a multitude of structural variants, and considerable cross-reactivity between receptors and their various ligands (Yayon, A., et al., *EMBO J.* 11: 1885–1890 (1992)). Though the carboxy-terminal region of the third immunoglobulin-like domain appears to be a structural element that defines specificity of different FGF members (Werner, et al., and Yayon, et al., cited above), the precise nature of FGF-receptor-heparin interactions and the protein residues involved have yet to be elucidated.

SUMMARY OF THE INVENTION

It is an objective of the invention to provide new structural analogues of fibroblast growth factors.

It is another objective of the invention to provide fibroblast growth factor analogues having binding and biological activities that are pharmacologically dissociated, i.e., that bind to an FGF receptor, which may be the same or different from a receptor that normally binds the wild-type factor, and/or exhibits different biological properties from that observed in the wild-type factor.

It is a further and more specific objective of the invention to provide fibroblast growth factor structural analogues such as structural analogues of human fibroblast growth factor-2, which have all or part of a surface loop replaced with another amino acid sequence.

These and other objectives are accomplished by the present invention which provides fibroblast growth factor structural analogues having amino acid changes in surface loops, or sequences adjacent to the surface loops, such that the overall secondary and tertiary structures of the polypeptides are not significantly perturbed, and the analogues bind to heparin. More particularly, this invention provides fibroblast growth factor structural analogues having an amino acid sequence replacement in the ninth or tenth β-strand of the factor, or the sequence that corresponds to the surface loop that connects the ninth and tenth β-strands, such that the interaction of β-strands nine and ten with adjacent strands is not significantly perturbed, and the analogue binds to heparin. The analogues exhibit binding affinity to a fibroblast growth factor receptor. Binding specificity of the analogues is preferably different from the binding specificity of the native factor to the corresponding receptor. In one embodiment, the analogue stimulates in vivo anglogenesis.

Preferred fibroblast growth factor structural analogues have an amino acid sequence substitution in the surface loop that extends from the ninth to the tenth β-strand. In some embodiments, all or part of the amino acid sequence in the growth factor surface loop extending from the ninth to the tenth β-strands is replaced by another amino acid sequence such as a corresponding amino acid sequence derived from related fibroblast growth factor or interleukin polypeptides.

Thus, the fibroblast growth factor analogues of this invention include, but are not limited to, analogues formed by using, in replacement of corresponding loop sequences in other growth factors, fibroblast growth factor-1 sequence Lys115-Lys116-His117-Ala118-Glu119-Lys 120-Asn121 (amino acids 115–121 of SEQ ID NO 2), fibroblast growth factor-2 sequence Arg118-Lys119-Tyr120-Thr 121-Ser122 (amino acids 118–122 of SEQ ID NO 1), fibroblast growth factor-3 sequence Arg-Leu-Tyr-Arg-Thr-Val-Ser-Ser-Thr-Pro-Gly-Ala-Arg-Arg-Gln-Pro-Ser-Ala-Glu-Arg-Leu (amino acids 132–152 of SEQ ID NO 4), fibroblast growth factor-4 sequence Tyr-Lys-Tyr-Pro-Gly (amino acids 172–176 of SEQ ID NO 5), fibroblast growth factor-5 sequence Ala-Ile-His-Arg-Thr-Glu-Lys-Thr-Gly-Arg-Glu (amino acids 176–186 of SEQ ID NO 6), fibroblast growth factor-6 sequence Asp-Leu-Tyr-Gln-Gly (amino acids 174–178 of SEQ ID NO 7), fibroblast growth factor-7 sequence Ala-Lys-Trp-Thr-His-Asn-Gly-Gly-Glu (amino acids 154–163 of SEQ ID NO 8), fibroblast growth factor-8 sequence Ala-Lys-Tyr-Glu-Gly (amino acids 144–148 of SEQ ID NO 9), and fibroblast growth factor-9 sequence Asn-Leu-Tyr-Lys-His-Val-Asp-Thr-Gly-Arg-Arg (amino acids 151–161 of SEQ ID NO 10). Analogues having loop flanking sequences changed, and peptide fragment analogues containing the loop sequences are correspondingly provided by the invention.

For example, human fibroblast growth factor-2 structural analogues having amino acid sequence substitutions in residues 112 to 128 result in factors that retain the same overall secondary and tertiary structure as FGF-2, but exhibit different biological properties. In these exemplary embodiments, an FGF-2 loop sequence is replaced with any size or composition of insert. Some derivatives are prepared by changing residues 115 to 124; others are prepared by changing loop residues 118 to 122. In one embodiment, for example, the FGF-2 loop is replaced with corresponding amino acids derived from FGF-1 from the same or another species; in another, an interleukin-1β from the same or another species is used; and, in another, a loop from FGF-7 from the same or another species is used. As summarized above, these analogues bind heparin and a native fibroblast growth factor receptor.

The invention also provides DNA encoding the fibroblast growth factor derivatives, biologically functional circular plasmid or viral DNA vectors comprising the DNA, and procaryotic or eucaryotic host cells such as *E. coli* transformed or transfected with the vectors in a manner allowing the host cell to express the new factors.

BRIEF DESCRIPTION OF THE FIGURES

FIG. 1 sets out sequence alignment of human FGF-2, FGF-1 and IL-1β in the loop region (identified in the Sequence Listing section hereinafter as ID NOs 1 to 3). The sequences underlined correspond to the surface loop located at the end of the ninth β-strand. The residues in parenthesis indicate the residues found in the bovine sequences.

FIG. 7 presents an amino acid sequence comparison among the nine members of the FGF family between residues corresponding to amino acid residues 113 and 128 in FGF-2 (SEQ ID NO 1; FGF-1 is set out as SEQ ID NO 2, and the other FGFs are sequentially set out as SEQ ID NOs 4 to 10, except that His121 of the FGF-1 bovine sequence is replaced by Asn in the human sequence). The numbering system is relative to FGF-2 and the asterisks refer to identical and conserved residues. Residues located between the FGF-2 locations Ser117 to Trp123 mark the positions where other FGFs contain inserts and changes. To illustrate homologous sequences in the ninth and tenth β-strands and in the loop region, the figure employs standard one-letter nomenclature for the amino acids: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

DETAILED DESCRIPTION OF THE INVENTION

Figure 2:
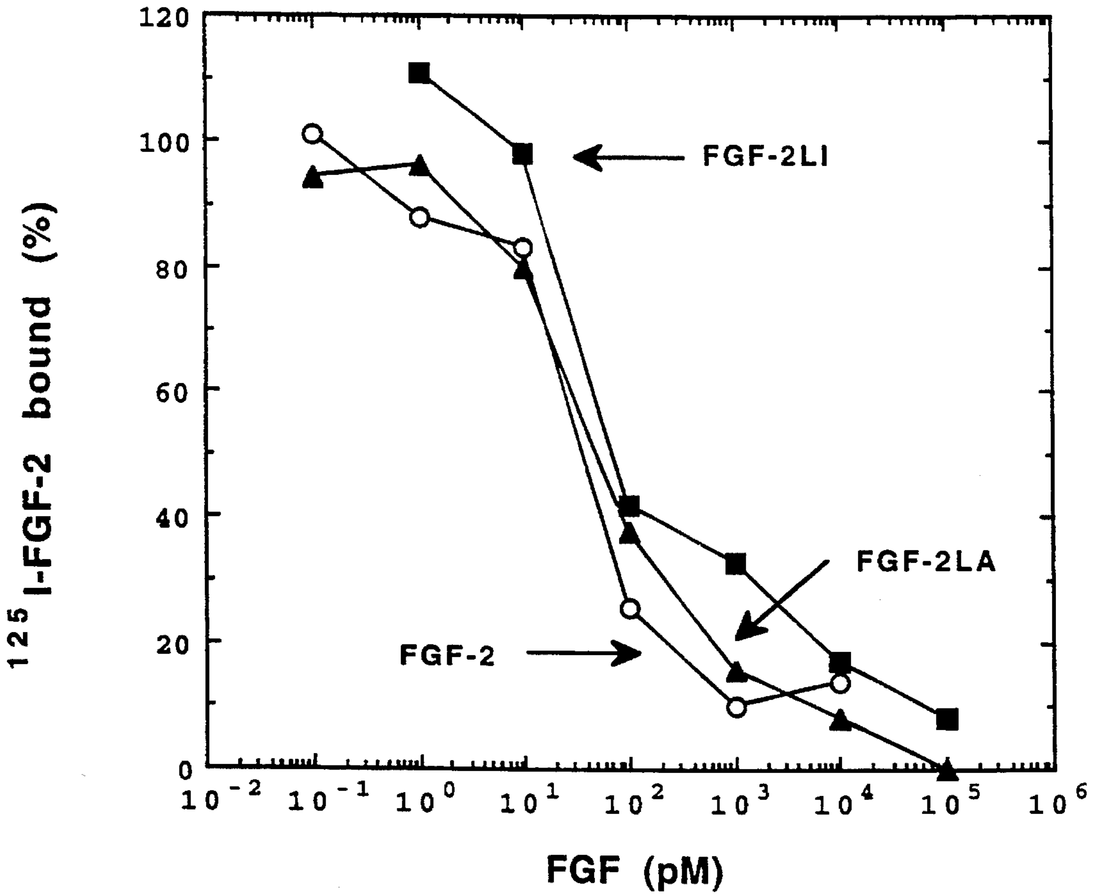
FIG. 2 plots competitive receptor binding of confluent baby hamster kidney cells incubated with $^{125}$I-FGF- 2 and indicated concentrations of competitors FGF-2 (open circles), structural analogue FGF-2LI (described in greater detail hereinafter, closed squares), and structural analogue FGF-2LA (described hereinafter, closed triangles).

This invention is based upon the finding that changes in fibroblast growth factor surface loop residues in a manner that does not perturb the overall secondary and tertiary structure of the FGF molecule yields an array of structural analogues having varied and desirable physiological properties, including FGF agonists and potential antagonists. Changes in loop sequences, or sequences adjacent to loop sequences, yield analogues that bind to heparin and exhibit binding affinity to a native fibroblast growth factor receptor.

By "antagonist" is meant any substance that tends to nullify the action of another, as one, for example, that binds to a cell receptor without eliciting a biological response. For FGFs, antagonists include, but are not limited to, any substance that binds to an FGF receptor but does not stimulate proliferation or migration of fibroblasts, endothelial cells and astroglial cells. In contrast, by "agonist" is meant any substance that has affinity for and stimulates physiological activity at cell receptors normally stimulated by naturally occurring factors, including mitogenic activity, angiogensis, chemotaxis, and the like. As used herein, the terms are not limiting, and a single factor may exhibit antagonism to one biological function mediated by native factor, and agonism to another function. Where this occurs, the biological activities of native factor are said to be pharmacologically dissociated in the analogue.

A protein is defined herein as a fibroblast growth factor (FGF) if it shows significant sequence and three-dimensional structural homology to other members of the FGF family, FGF-like activity in in vitro or in vivo assays and binds to heparin or heparin-like substances. By "heparin" is meant the heterogeneous, sulfated anionic polysaccharide composed of D-glucuronic acid and D-glucosamine, bound to a protein core as the "proteoglycan" or in a free form as the "aglycan", that may or may not have anticoagulant properties. "Heparin-like" substances are molecules that have oligosaccharide structures related to the heparins, but may or may not have anticoagulant activity. Any type of fibroblast growth factor or mutein or derivative is encompassed by this invention, particularly human fibroblast growth factor, as well as loop sequence peptides that exhibit antagonist or agonist properties, or both.

Broadly speaking, the fibroblast growth factor analogues of this invention include structural analogues of fibroblast growth factor having at least one amino acid deletion, insertion or replacement in a β-strand, or a loop connecting two β-strands such that adjacent strands are not perturbed, and the molecule retains its overall secondary and tertiary structure. Secondary and tertiary structure is determined by heparin binding, binding to an FGF receptor, spectroscopy (using ultraviolet, visible, or circular dichroic light), X-ray crystallography, and biological activities.

Particularly preferred are FGF sequence replacements in a loop connecting two β-strands, analogous to the structural cassette or module replacements of turns with retention of parent conformation disclosed for enzymes by Hynes, T. R., et al., *Nature* 339: 73–76 (1989). In some embodiments, the ninth or tenth β-strand of the factor, or the sequence that corresponds to the surface loop that connects the ninth and tenth β-strands, are replaced with any size or composition amino acid sequence insert such that overall molecular folding is not significantly perturbed. In certain embodiments, the surface loop is replaced with a surface loop from another factor. Thus, this invention specifically encompasses loop and loop stem and anchor replacements with structurally related and unrelated sequences, including random loops, longer or shorter loops, and differently charged loops and their stems and anchors. It also encompasses peptide fragments that mimic these loops in binding studies and biological assays.

As set out more fully below, numbering of the amino acids in these strands is, for convenience, made with reference to FGF-2. Perturbation and strand adjacency are herein defined in a three-dimensional sense and measured as described above. Overall folding is maintained in the analogues. Preferred analogues bind to an FGF receptor with an affinity that is greater than, or up to 100-times lower than the binding of a corresponding native FGF family member exhibiting affinity to the receptor.

Receptors that many of the analogues typically bind include native baby hamster kidney (BHK) cell fibroblast growth factor receptor, NIH 3T3 cell receptors, or other receptors specific to particular FGFs. Binding preferably exhibits an affinity substantially similar or superior to the binding of the corresponding native factor to that receptor. An advantage of the invention is that the loop manipulation results in analogues exhibiting similar binding profiles to the corresponding factors from which the loops are derived. Thus, certain analogues of the invention target receptors that the native factor does not bind, including receptors on different cell types. For example, factors that ordinarily bind to endothelial cell receptors can be engineered to bind to epithelial cell receptors, and so forth. Examples are given hereinafter. One embodiment stimulates angiogenic activity in vivo.

Especially preferred structural analogues are those in which the factor has at least one amino acid deletion, addition or substitution in the sequence of the surface loop that extends from the ninth to the tenth β-strand and protrudes from the surface when the molecule is folded as described by Eriksson, et al., Zhu, et al., and Zhang, et al., cited above, and has the overall secondary and tertiary structure of the native factor. In some embodiments, the replacements are sequences from other FGF species or related molecules. In other embodiments, the replacements are structurally unrelated to any FGF species, and may contain fewer or more amino acids, or differently charged amino acids. Thus, any amino acid sequence can be used as a sequence replacement in the loop connecting the strands.

For example, structural FGF analogues of the invention include analogues having at least one amino acid deletion, addition or substitution, particularly amino acid sequence substitution, in surface loops that include, but are not limited to, fibroblast growth factor-1 sequence 112 to 123, particularly Lys115-Lys116-His117-Ala 118-Glu119-Lys120-Asn121 (amino acids 115–121 of SEQ ID NO 2); fibroblast growth factor-2 sequence 115 to 124, particularly Arg118-Lys119-Tyr120-Thr121-Ser122 (amino acids 115–124 of SEQ ID NO 1), fibroblast growth factor-3 sequence Arg-Leu-Tyr-Arg-Thr-Val-Ser-Ser-Thr-Pro-Gly-Ala-Arg-Arg-Gln-Pro-Ser-Ala-Glu-Arg-Leu (amino acids 132–152 of SEQ ID NO 4), fibroblast growth factor-4 sequence Tyr-Lys-Tyr-Pro-Gly (amino acids 172–176 of SEQ ID NO 5), fibroblast growth factor-5 sequence Ala-Ile-His-Arg-Thr-Glu-Lys-Thr-Gly-Arg-Glu (amino acids 176–186 of SEQ ID NO 6), fibroblast growth factor-6 sequence Asp-Leu-Tyr-Gln-Gly (amino acids 174–178 of SEQ ID NO 7), fibroblast growth factor-7 (also known as keratinocyte growth factor or KGF) sequence Ala-Lys-Trp-Thr-His-Asn-Gly-Gly-Glu (amino acids 154–162 of SEQ ID NO 8), fibroblast growth factor-8 sequence Ala-Lys-Tyr-Glu-Gly (amino acids 144–148 of SEQ ID NO 9), and fibroblast growth factor-9 sequence Asn-Leu-Tyr-Lys-His-Val-Asp-Thr-Gly-Arg-Arg (amino acids 151–161 of SEQ ID NO 10). A comparison of surface loop sequences in the FGF family is depicted in FIG. 7. In these embodiments of the invention, structural analogues are prepared by replacing the surface loop sequence of one FGF with another amino acid sequence such as, but not limited to, a surface loop sequence from another factor.

Changes in neighboring regions that affect the loop, including loop stems and anchor points, are encompassed by the invention, so long as the overall folding of the molecule is not perturbed. Thus, analogues of the invention include structures having mutations, particularly sequence replacements, in fibroblast growth factor-1 sequence Tyr112-Ile113-Ser114-Lys115-Lys116-His117-Ala 118-Glu119-Lys120-Asn121-Trp122-Phe123-Val124-Gly125 (amino acids 112–125 of SEQ ID NO 2), fibroblast growth factor-2 sequence Tyr115-Arg116-Ser117-Arg118-Lys119-Tyr 120-Thr121-Ser122-Trp123-Tyr124 (amino acids 115–124 of SEQ ID NO 1), fibroblast growth factor-3 sequence Tyr-Ala-Ser-Arg-Leu-Tyr-Arg-Thr-Val-Ser-Ser-Thr-Pro-Gly-Ala-Arg-Arg-Gln-Pro-Ser-Ala-Glu-Arg-Leu-Trp-Tyr (amino acids 129–154 of SEQ ID NO 4), fibroblast growth factor-4 sequence Tyr-Glu-Ser-Tyr-Lys-Tyr-Pro-Gly-Met-Phe (amino acids 169–178 of SEQ ID NO 5), fibroblast growth factor-5 sequence Tyr-Ala-Ser-Ala-Ile-His-Arg-Thr-Glu-Lys-Thr-Gly-Arg-Glu-Trp-Tyr (amino acids 173–188 of SEQ ID NO 6), fibroblast growth factor-6 sequence Tyr-Glu-Ser-Asp-Leu-Tyr-Gln-Gly-Thr-Tyr (amino acids 171–180 of SEQ ID NO 7), fibroblast growth factor-7 sequence Tyr-Ala-Ser-Ala-Lys-Trp-Thr-His-Asn-Gly-Gly-Glu-Met-Phe (amino acids 151–164 of SEQ ID NO 8), fibroblast growth factor-8 sequence Asn-Asn-Tyr-Thr-Ala-Leu-Gln-Asn-Ala-Lys-Tyr-Glu-Gly-Trp-Tyr-Met-Ala-Phe-Thr-Arg-Lys (SEQ ID NO 9), and fibroblast growth factor-9 sequence Asn-Trp-Tyr-Asn-Thr-Tyr-Ser-Ser-Asn-Leu-Tyr-Lys-His-Val-Asp-Thr-Gly-Arg-Arg-Tyr-Tyr-Val-Ala-Leu-Asn-Lys-Asp (SEQ ID NO 10). The invention also encompasses peptides corresponding to these loops that exhibit heparin and FGF receptor binding.

Structural analogues of FGF-2 are preferred in some embodiments. By "FGF-2" is meant any fibroblast growth factor-2 exhibiting biologic activity including the 146-amino acid polypeptide originally isolated and sequenced, the 154 amino acid form currently thought to be the full polypeptide, truncated forms exhibiting activity, extended forms such as placental FGF, higher molecular weight N-terminally extended forms described in the literature and analogues including derivatives and muteins of any of these. The term specifically includes natural FGF-2 extracted from mammalian tissue as well as recombinant polypeptides expressed from cloned DNA in *E. coli* or *S. cervisiae* from any species or expressed in insect or mammalian cells with appropriate vectors.

Human FGF-2 is preferred in many embodiments. Human FGF-2 having 9th or 10th β-strands which can be manipulated according to the invention includes, but is not limited to, FGF-2 having amino acid additions, amino acid substitutions, and amino acid deletions, including deletions of portions of the amino or carboxyl terminus, and chimeric proteins containing FGF at the N-or C-terminus of another protein. Example FGF-2s which can be manipulated according to the invention include those having cysteine substituted with a neutral amino acid such as serine, or aspartic acid, arginine, glycine, serine, or valine substituted with other acids suggested to have enhanced stability in Eur. Pat. Ap. Pub. No. 281,822 to Seno, et al.; muteins formed by replacing at least one, and more preferably two, of the cysteines found in natural FGF-2 with a different amino acid residue to yield a more stable analogue (Eur. Pat. Ap. Pub. No. 320,148 to Arakawa and Fox); muteins lacking amino acids from the carboxyl terminus and, optionally, having amino acid replacements suggested to have improved stability while retaining activity in Eur. Pat. Ap. Pub. No. 326,907 to Seno, et al.; mutants lacking a substantial part of the amino-or carboxyl-terminus such as those described by Seno, et al., *Eur. J. Biochem.* 188: 239–245 (1990); muteins having various point mutations or an N-terminal deletion suggested in Eur. Pat. Ap. Pub. No. 298,723 to Fiddes, et al.; the M1-bFGF to M6-bFGF muteins containing missing and substituted amino acids disclosed in Eur. Pat. Ap. Pub. No. 363,675 to Bergonzoni, cited above; readily expressed FGF prepared by replacement of Ala-3 and Ser-5 of recombinant FGF with Glu as described in Seddon, A. P. et al., *Annals N.Y. Acad. Sci.* 638: 98–108 (1991) and analogues thereof; and the like.

In the practice of this invention, a fibroblast growth factor derivative of this invention such as a human FGF-2 structural analogue is prepared by deleting, adding to, or substituting at least one amino acid, preferably more than one amino acid, in the sequence between residues 112 (Tyr) and 128 (Lys). In some embodiments, the substitution occurs between residues 115 (Tyr) and 124 (Tyr); in others, the change occurs between 118 (Arg) and 122 (Ser). As defined above, the numbering convention for other FGF analogues is relative to FGF-2.

In some preferred embodiments, fibroblast growth factor structural analogues have an amino acid sequence replacement in the ninth or tenth β-strand of the factor, or the sequence that corresponds to the surface loop that connects the ninth and tenth β-strands. Amino acid sequences are herein defined as a sequence of at least three amino acids, typically at least five amino acids. Exemplary amino acid sequences are set out above.

For example, a fibroblast growth factor structural analogue such as a human FGF-2 structural analogue is prepared by replacing all or part of the amino acid sequence in the 9th to 10th β-strand surface loop with a random amino acid sequence of any length, provided that the overall folding of the molecule is not significantly perturbed. Thus, a sequence derived from a structurally related polypeptide such as fibroblast growth factor-2 from another species, human fibroblast growth factor-1, or 3 to 9, fibroblast growth factor-1, or 3 to 9 from another species, human interleukin-1α or β, or interleukin- 1α or β from another species, soybean trypsin inhibitor or hisactophilin, may be employed. In some embodiments, preferred FGF-2 analogues involve an amino acid replacement that eliminates phosphorylation at Thr121.

In one embodiment, a structural analogue of this invention exhibiting desirable biological properties more particularly described below comprises a fibroblast growth factor-2 derivative having surface loop amino acids Arg118-Lys119-Tyr120-Thr121-Ser122 (amino acids 118–122 of SEQ ID NO 1) replaced with corresponding amino acid sequence Ala115-Gln116-Phe117-Pro118-Asn119 (amino acids 231–235 of SEQ ID NO 3) from human interleukin-1β, denoted FGF-2LI in the Examples that follow (SEQ ID NO 15). In another embodiment, the analogue comprises a human fibroblast growth factor-2 derivative having surface loop amino acids Arg118-Lys119-Tyr120-Thr121-Ser122 (amino acids 118–122 of SEQ ID NO 1) replaced with corresponding amino acid sequence Lys115-Lys116-His117-Ala118-Glu 119-Lys120-His121 (amino acids 115–121 of SEQ ID NO 2) derived from bovine FGF-1, denoted FGF-2LA in the Examples that follow (SEQ ID NO 16). In yet another embodiment, the analogue comprises a human fibroblast growth factor-2 derivative having surface loop amino acids 118 to 122 replaced with a corresponding 9-residue amino acid loop sequence from FGF-7 (also known as Keratinocyte Growth Factor), Ala-Lys-Trp-Thr-His-Asn-Gly-Gly-Glu from FGF-7 (residues 154–162 of SEQ ID NO 8).

The novel fibroblast growth factor structural analogues of this invention are prepared by point mutations, sequence alterations or polypeptide assembly from constituent amino acids or peptides using chemical, biochemical or physical means known to those skilled in the art. Alternatively, the novel fibroblast growth factor analogues of this invention are prepared by recombinant protein synthesis involving preparation of DNA encoding a surface loop mutein, insertion of that DNA into a vector, expression of the vector in host cells, and isolation of the mutant FGF thereby produced.

DNA encoding the FGF structural analogues of this invention are prepared by altering a gene of fibroblast growth factor by nucleotide deletions, nucleotide additions, or point mutations produced using standard means. Illustrations are set out in Examples 1 and 2. Because of the degeneracy of the genetic code, a variety of codon change combinations can be selected to form DNA that encodes the FGF analogues of this invention, so that any nucleotide deletion(s), addition(s), or point mutation(s) that result in a DNA encoding loop mutant FGF are encompassed by this invention. Since certain codons are more efficient for polypeptide expression in certain types of organisms, the selection of fibroblast gene alterations to yield DNA material that codes for the FGF muteins of this invention are preferably those that yield the most efficient expression in the type of organism which is to serve as the host of the recombinant vector. Altered codon selection may also depend upon vector construction considerations.

Fibroblast growth factor DNA starting material which is altered to form DNA coding for the FGF analogues of the invention may be natural, recombinant or synthetic. Thus, DNA starting material is isolated from tissue or tissue culture, constructed from oligonucleotides using conventional methods, obtained commercially, or prepared by isolating RNA coding for FGF from fibroblasts, and using this RNA to synthesize single-stranded cDNA which is used as a template to synthesize the corresponding double stranded DNA.

Illustrating the present invention are cloned complementary DNA sequences defining human FGF-2 analogues such as that constructed in Examples 1 and 2. Also encompassed are DNA sequences homologous or closely related to complementary DNA described herein, namely DNA sequences which hybridize, particularly under stringent conditions that result in pairing only between nucleic acid fragments that have a high frequency of complementary base sequences, to FGF analogue cDNA, and RNA corresponding thereto. In addition to the FGF-encoding sequences, DNA encompassed by this invention may contain additional sequences, depending upon vector construction sequences, that facilitate expression of the gene.

DNA encoding the FGF analogues of this invention, or RNA corresponding thereto, are then inserted into a vector, e.g., a pBR, pUC, pUB or pET series plasmid, and the recombinant vector used to transform a microbial host organisms. Host organisms useful in the invention are bacterial (e.g., *E. coli* or *B. subtilis*), yeast (e.g., *S. cervisiae*), mammalian (e.g., mouse fibroblast), or insect cells. This invention thus also provides novel, biologically functional viral and circular plasmid RNA and DNA vectors incorporating RNA and DNA sequences describing the FGF analogues generated by standard means. Culture of host organisms stably transformed or transfected with such vectors under conditions facilitative of large scale expression of the exogenous, vector-borne DNA or RNA sequences and isolation of the desired polypeptides from the growth medium, cellular lysates, or cellular membrane fractions yields the desired products. An example of expression of FGF-2 muteins in *E. coli* is given in Example 3.

The present invention provides for the total and/or partial manufacture of DNA sequences coding for FGF-2 loop mutants, and including such advantageous characteristics as incorporation of codons preferred for expression by selected non-mammalian hosts, provision of sites of cleavage by restriction by endonuclease enzymes, and provision of additional initial, terminal or intermediate DNA sequences which facilitate construction of readily expressed vectors. Correspondingly, the present invention provides for manufacture (and development by site specific mutagenesis of cDNA and genomic DNA) of DNA sequences coding for microbial expression of FGF analogues which differ from the forms specifically described herein in terms of identity or location of one or more amino acid residues (i.e., deletion analogues containing less than all of the residues specified for human FGF-2, and/or substitution analogues wherein one or more residues are added to a terminal or medial portion of the polypeptide), and which share the biological properties of FGF-2 analogues described herein.

DNA (and RNA) sequences of this invention code for all sequences useful in securing expression in procaryotic or eucaryotic host cells of polypeptide products having at least a part of the primary structural conformation, and one or more of the biological properties of FGF analogues which are comprehended by: (a) the DNA sequences encoding FGF-2 loop muteins as described herein, or complementary strands; (b) DNA sequences which hybridize to DNA sequences defined in (a) or fragments thereof; and (c) DNA sequences which, but for the degeneracy of the genetic code, would hybridize to the DNA sequences defined in (a) and (b) above. Specifically comprehended are genomic DNA sequences encoding allelic variant forms of FGF analogues included therein, and sequences encoding loop mutein RNA, fragments thereof, and analogues wherein RNA or DNA sequences may incorporate codons facilitating transcription or RNA replication of messenger RNA in non-vertebrate hosts.

Isolation and purification of microbially expressed polypeptides provided by the invention are by conventional means including, for example, preparative chromatographic separations such as that illustrated Example 3, and immunological separations, including monoclonal and/or polyclonal antibody preparations.

As summarized adore and described in detail in the Examples below, two example FGF-2 structural analogues of this invention are FGF-2LA (SEQ ID NO 16) and FGF-2LI (SEQ ID NO 15), FGF-2 sequences having loop residues 118 to 122 replaced by corresponding sequences from bovine FGF-1 and human interleukin-1βrespectively, expressed in *E. coli.* These mutations have no apparent effect on either heparin binding, estimated by the concentration of NaCl required to elute the protein from heparin Sepharose, or on the ability of the proteins to compete with $I^{125}$-FGF-2 binding to the FGF receptors present on baby hamster kidney cells and NIH 3T3 cells (Example 4). The loop analogues are mitogenically active in bovine endothelial cell proliferation assays. Both analogues exhibit significantly reduced capability to induce urokinase-type plasminogen activator. In an in vitro angiogenesis assay, FGF-2LA exhibits capillary-like tube formation comparable to wild-type FGF-2. In the same in vitro assay, FGF-2LI exhibits much less induction of capillary-like structures, but it significantly stimulates anglogenesis in an in vivo assay.

Another FGF-2 loop mutant, FGF-2LK (described in greater detail in the Examples), contains a 9-amino acid sequence from FGF-7 (Keratinocyte Growth Factor). FGF-2 does not bind to FGF-7 receptor (FGFR2 IIIb) on keratinocytes, and FGF-7 does not bind to FGF receptor type 1 (FGFR1). Replacement of the loop sequence in FGF-2 with that from FGF-7 results in an apparent decrease in the affinity of the protein to heparin. In receptor binding experiments, the FGF-2LK protein is unable to displace or compete with binding of FGF-2 to FGF receptor type 1, but competes with FGF-7 to receptor type 2 (IIIb) whereas FGF-2 does not compete with binding. Thus, the loop sequence confers receptor-ligand specificity and allows for the binding of FGF-2LK mutant to a receptor subtype (FGFR IIIb) that binds FGF-7 but not FGF-2. Conversely, the loop sequence from FGF-7 abolishes binding of the protein to FGF receptor 1.

Introduction of new primary structural elements in the FGF surface loop without significantly perturbing the overall secondary and tertiary structure of the molecule provides an array of FGF structural analogues that give rise to altered properties from one FGF type to another, and thus a means to modulate the activities of FGF proteins, a means to pharmacologically dissociate the biological activities of the proteins, and a means to introduce new activities. As illustrated in the Examples that follow, FGF loop analogues can be structured to bind to the same receptors as corresponding native FGF, or to different receptors, particularly to receptors corresponding to the loop rather than to the native FGF.

FGF antagonists exhibiting reduced biological activity are useful as anticancer and antiproliferative agents. The antagonists that act as angiogenesis inhibitors are useful for the treatment of diseases where neovascularization is dominant in the pathology such as retinopathies of the eye, neovascular glaucoma, skin disorders, chronic inflammation, rheumatoid arthritis, and the like.

FGF loop structural analogues that are agonists of FGF activity can promote vascularization, cell growth, and/or cell survival, and thus have application in tissue repair such as healing of wounds, burns, bone fractures, surgical abrasions, gastrointestinal ulcers, and the like as well as tissue repair during ischemia and myocardial infarction via neovascularization of ischemic tissue.

In addition to surface loop amino acid sequence replacements, this invention further provides growth factor peptide antagonists constructed to mimic the placed loop, i.e., that bind to FGF receptors but do no stimulate proliferation or migration of fibroblasts and other cells stimulated by the corresponding factors containing the loop.

Expression of FGF receptor type is cell-specific, and the type of receptor expressed determines which FGF the cell will respond to. As mentioned above, change receptor specificity, such as that seen for FGF-2LA, indicates that FGF-2 can be engineered to target a cell type that it normally does not interact with, such as an epithelial cell rather than an endothelial cell.

The following examples are presented to further illustrate and explain the present invention and should not be taken as limiting in any regard.

EXAMPLE 1

This example illustrates the construction of a human FGF-2 structural analogue denoted FGF-2LI (SEQ ID NO 15) having the surface loop (residues 118 to 122) of FGF-2 replaced with the corresponding amino acids derived from interleukin-1β (IL-1β).

A gene encoding human glu$^{3,5}$FGF-2 is first prepared as described in Seddon, A. P. et al., cited above, herein incorporated in its entirety by reference, and cloned into a T7 expression vector, pET-3a(M13). Briefly stated, a synthetic gene encoding the 155 amino acid form of human FGF-2 cloned into pUC 18 is purchased from British Bio-technology, Oxford, UK. The nucleotide sequence (2– 49) to be changed is excised from pUC 18 with HindIII and BspMII and a synthetic fragment encoding the first 5 N-terminal amino acids of FGF-1 and containing an internal Nde1 site is cloned into pUC 18, yielding a construct encoding glutamic acid at positions 3 and 5. The cDNA encoding FGF-2 is then excised from pUC 18 with Nde1 and BamH1 and cloned into the Nde1 and BamH1 restriction endonuclease sites of the expression vector pET-3a(M13), a derivative of pET-3a.

Two unique restriction endonuclease sites, BstB1 and Spl1, are introduced into the gene in such a way as to produce no change in the encoded amino acids (i.e., silent mutations) at positions that flank the codons encoding the segment Ser117-Trp123 of FGF-2 (FIG. 1).

Replacement of residues Arg118-Lys119-Tyr120-Thr121-Ser 122 of FGF-2 (amino acids 118–122 of SEQ ID NO 1) with the human sequence Ala115-Gln116-Phe117-Pro118-Asn119 (amino acids 231–235 of SEQ ID NO 3) from the corresponding loop of the structural analogue IL-1β (115–119) (FIG. 1) is then effected. The plasmid DNA is subjected to BstB1 and Spl1 digestion and the larger DNA fragment, isolated using agarose gel electrophoresis. The DNA fragment is ligated using T4 DNA ligase to a double-stranded DNA obtained by annealing two synthetic oligonucleotides, 5'-CGAACGATTG GAATCTAATA ACTACAATAC GTACCGGTCT GCGCAGTTTC CTAACTGGTA TGTGGCACTT AAGC-3' (SEQ ID NO 11) and 5'-GTACGCTTAA GTGCCACATA CCAGTTAGGA AACTGCGCAG ACCGGTACGT ATTGTAGTTA TTAGATTCCA ATCGTT-3' (SEQ ID NO 12), that contain termini compatible to those generated by BstB1 and Spl1 digestion. The ligation product is used to transform strain DH5α *E. coli* cells. The desired mutant plasmid is selected for on the basis of susceptibility to cleavage at the newly introduced Afl2 restriction site (underlined) and confirmed by complete sequencing of the gene. The plasmid in *E. coli* was deposited in the American Type Culture Collection, 12301 Parklawn Drive, Rockville, Md. 20852 U.S.A. and bears A.T.C.C. accession number 69417.

EXAMPLE 2

This example illustrates the construction of a human FGF-2 structural analogue denoted FGF-2LA (SEQ ID NO 16) having the surface loop (residues 118 to 122) of FGF-2 replaced with the corresponding amino acid sequence derived from FGF-1 (FIG. 1).

Replacement of the segment Arg118-Ser122 of FGF-2 with the bovine sequence Lys115-Lys116-His117-Ala118-Glu 119-Lys120-His121 (amino acids 115–121 of SEQ ID NO 2; Asn in the human sequence) corresponding to the surface loop 115–121 of FGF-1 (see FIG. 1) is accomplished as described in Example 1 above using the following annealed synthetic mutagenic oligonucleotides: 5'-CGAACGATTG GAATCTAATA ACTACAATAC GTACCGGTCT AAAAAGCATG CTGAAAAACA CTGGTATGTG GCACTTAAGC-3' (SEQ ID NO 13) AND 5'-GTACGCTTAA GTGCCACATA CCAGTGTTTT TCAGCATGCT TTTTAGACCG GTACGTATTG TAGTTATTAG ATTCCAATCG TT-3' (SEQ ID NO 14). The desired mutant plasmid is selected on the basis of the susceptibility to cleavage at the newly introduced Sph1 restriction site (underlined) and confirmed by complete sequencing of the gene.

EXAMPLE 3

FGF-2LA and FGF-2LI mutants constructed in Examples 1 and 2 are expressed and purified in this Example.

Following sequence verification, the plasmids containing FGF-2 loop mutants described in Examples 1 and 2 above are transformed into competent *E. coli* BL21 plys S and cultured at 37° C. in Luria broth containing 50 μg/ml ampicillin and 30 μg/ml chloramphenicol until an absorbance at 600 nm of 0.4 is reached. Expression of the recombinant protein is induced by the addition of 2 mM isopropylthiogalactoside for 2 hours at 37° C.

Cells from 1 liter cultures are harvested by centrifugation, resuspended in 30 ml of 50 mM Tris-HCl, pH 7.5 containing 0.1 mM EDTA and 0.6M NaCl, and disrupted by treatment with lysozyme (10 μg/ml) for 20 min at 4° C. followed by sonication (6×30 sec pulses). The lysates are clarified by centrifugation (10,000×g; 20 min) and the supernatant solutions incubated with 5 ml of hydrated heparin Sepharose (Pharmacia/LKB) at 4° C. for 1 hour with constant rotation. The resin is isolated by filtration on 0.8 μm filter apparatus (Nalgene), washed extensively with 10 mM Tris-HCl pH 7.4 containing 0.6M NaCl and bound protein eluted with Tris buffer containing 3M NaCl (25 ml). The 3M NaCl eluent is diluted 6-fold with Tris buffer and loaded onto a TSK heparin 5PW column (0.21× 15 cm; The Nest Group, MA) and the column developed using a linear NaCl gradient (0.6 to 2M) in 90 min at a flow rate of 3 ml/min.

The FGF-2 species purified on the heparin column are analyzed using reverse phase high performance liquid chromatography ($C_4$, Vydac, the Separations Group, Hesperia, Calif.) using a 0.1% trifluoroacetic acid/acetonitrile gradient (28 to 48% $CH_4CN$ in 60 min) at a flow rate of 0.7 ml/min. Elution of bound material is monitored at 210 nm. Both FGF-2LA and FGF-2LI are found to be homogenous, each giving a single peak. Purity and molecular weight determinations are also made using a silver stain detection system (Phastgel System, Pharmacia, LKB), and each protein yielded a single 18 kD silver stained band by SDS-PAGE.

N-terminal sequence analyses of reversed phase purified proteins are performed on a model 477A pulsed-liquid phase sequencer equipped with a Model 120A on-line phenylthiohydantoin-derivative analyzer (Applied Biosystems, Forster City, Calif.). The analysis gives the sequences Ala-Glu-Gly-Glu-Ile-Thr-Thr-Leu-Pro-Ala (87%; amino acids 2– 11 of SEQ ID NO 15) and Met-Ala-Glu-Gly-Glu-Ile-Thr-Thr-Leu-Pro-Ala (13%; amino acids 1–11 of SEQ ID NO 15), indicating a small fraction of the protein retains the N-terminal methionyl residue (introduced for the expression of the mature form of the protein).

Amino acid compositions are determined after HCl gas phase hydrolysis (5.7M HCl/0.1% phenol, 24 hours at 110° C.) using a model 420A phenylisothiocyanate-derivatizer equipped with an on-line model 130A separation system (Applied Biosystems). The full sequences of human FGF-2LA and FGF-2LI are given in the Sequences Listing section which appears hereinafter (SEQ ID NOs 15 and 16).

FIG. 7 illustrates an amino acid sequence comparison between the nine members of the FGF family between residues 88 and 143 using a numbering system relative to FGF-2. The asterisks refer to identical and conserved residues. The proteins exhibit 36 other sites of identical and conserved residues in addition to the 7 denoted.

EXAMPLE 4

This example describes binding and cell proliferation studies using the FGF-2 mutants isolated and purified in Example 3 above.

The affinities of FGF-2LA and FGF-2LI for immobilized heparin are identical to wild type FGF-2 on elution from a TSK-heparin column at about 1.5M NaCl.

FGF-2LI and FGF-2LA are tested for their capacity to compete for the binding of $^{125}$I-FGF-2 (Amersham Corp.) to baby hamster kidney (BHK) cells, which express high numbers of FGF receptor. The assay employed is described by Moscatelli (*J. Cell. Physiol.* 131: 123–130 (1987)). Briefly stated, BHK cells plated on 24-well plates are incubated with 50 pM $^{125}$I-FGF-2 with serial dilutions of unlabelled FGF-2, FGF-2LI or FGF-2LA loop mutants at room temperature for 1 hour or at 4° C. for 2 hours. The cells are then incubated at 4° C. for 30 minutes, washed twice with phosphate-buffered saline and treated with 20 mM HEPES (N-2-hydroxyethyl-piperazine-N'-2-ethanesulfonic acid), pH 7.5, containing 2M NaCl to remove $^{125}$I-FGF-2 bound to low affinity heparin sulfate binding sites. Receptor bound $^{125}$I-FGF-2 is recovered by treatment of the cells with 0.5% Triton X-100 in 0.1M sodium phosphate, pH 8, and counted in a γ-counter. Assays are conducted in duplicate.

The results of this binding assay, plotted in FIG. 2, are found to be similar for FGF-2, FGF-2LA and FGF- 2LI. Replacement of FGF-2 sequence 118–122 with the corresponding IL-1β or FGF-1 sequences has no apparent effect on the capacities of the mutant proteins to compete with $^{125}$I-FGF-2 binding to high affinity cell membrane FGF type I receptors present on BHK cells. Since the mutants contain FGF-1 and IL-1β sequences, IL-1β and FGF-1 are tested in the BHK cell FGF-receptor binding assay. FGF-1 binds to BHK cell FGF receptors with an affinity equal to that of FGF-2, whereas no binding for hrIL-1β (Biogen) is detected.

Figure 3:
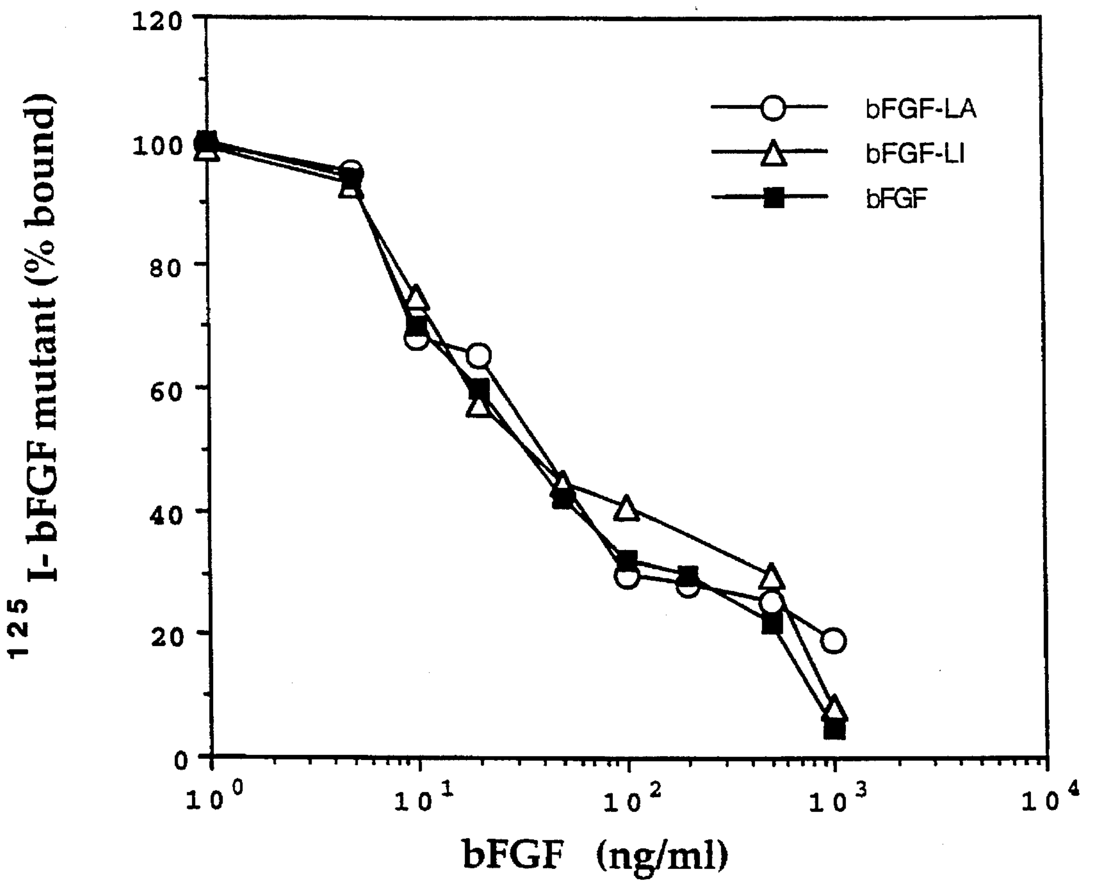
FIG. 3 plots the binding of radioiodinated FGF-2 (closed squares), FGF-2LA (open circles), and FGF-2LI (open triangles) to FGF-receptor type 1 present on NIH 3T3 cells as a function of added unlabelled FGF proteins.

FIG. 3 shows the binding of radioidinated FGF-2 (bFGF), FGF-LA and FGF-LI to FGF-receptor type 1 presented on NIH 3T3 cells as a function of added unlabelled FGF proteins using these procedures. The data show that the competition binding curves for FGF-LA and FGF-LI are identical to that for FGF-2, and demonstrate that the loop exchanges in FGF-2 have no impact on the receptor binding properties of the proteins to cell surface FGF receptor type 1 (FGFR1).

The mitogenic activity of FGF-2, FGF-2LI and FGF-2LA are determined using bovine vascular endothelial cells derived from adult aortic arch as previously described (Gospardarowicz, D., et al., *Proc. Nat. Acad. Sci.* 81: 6963–6967 (1984)). Briefly, cells are seeded at an initial density of $0.8\times10^4$ cells per 24-well plate in 0.5 ml Dulbecco's modified Eagle's medium (DMEM) containing 10% calf serum (Hyclone, Logan, Utah) supplemented with penicillin (100 units/ml), streptomycin (100 ug/ml) and L-glutamine (2 mM). Two hours after plating, 20 ul aliquots of serial dilutions of FGF-2 and the mutants in DMEM are added. Inhibition of FGF-2-stimulated growth was determined at a fixed concentration of FGF-2, while that of the mutant proteins is varied. After 5 days in culture, duplicate plates are trypsinized and cell densities determined by cell counting in a Coulter counter. Determinations are conducted in duplicate.

Figure 4:
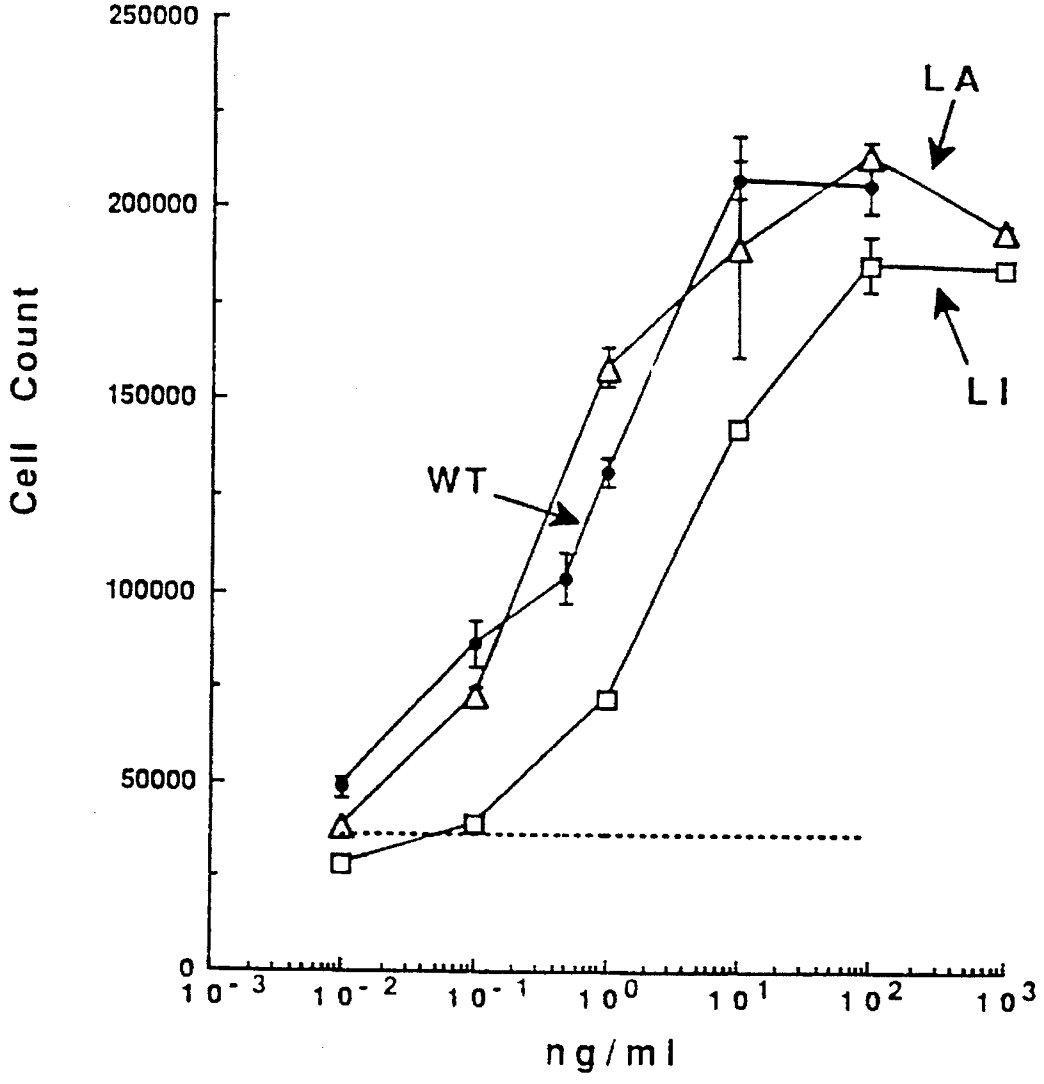
FIG. 4 shows endothelial cell growth of adult bovine aortic arch endothelial cells plated at 8000 cells/well and incubated for 5 days with the indicated concentrations of FGF-2 (closed circles), FGF-2LI (open squares), and FGF-2LA (open triangles).

The results of this cell proliferation assay are plotted in FIG. 4. The dashed line indicates basal cell growth in the absence of added FGF-2. Closed circles indicate stimulation by FGF-2. FGF-2LI mutant is represented by open squares and FGF-2LA mutant by open triangles. FGF-2LI is about 5 to 10 times less potent than FGF-2, whereas FGF-2LA is as potent as the wild-type factor.

EXAMPLE 5

This example describes in vitro and in vivo angiogenesis studies using the FGF-2 mutants isolated and purified in Example 3 above.

Figure 5:
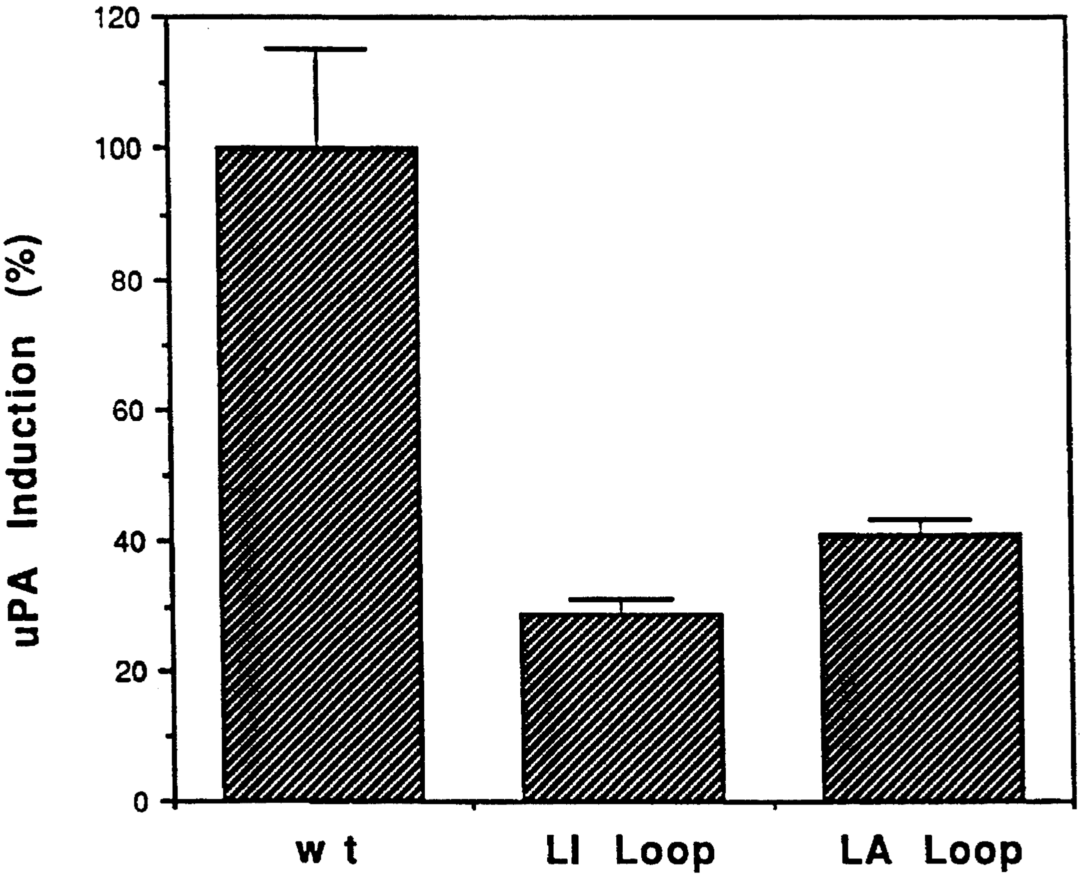
FIG. 5 is a bar graph depicting production of cell-associated urokinase-type plasminogen activator induced by wild-type or mutant FGF-2 (10 ng/ml).

Urokinase-type plasminogen activator induction by the FGF mutants is evaluated. Adult bovine aortic endothelial (ABAE) cells are seeded at 20,000 cells/well in 96-well plates and maintained in DMEM containing 10% calf serum (Hyclone, Logan, Utah) supplemented with penicillin (100 units/ml), streptomycin (100 μg/ml) and L-glutamine (2 mM) and different concentrations of FGF-2 or mutants. After 24 hours, the cells are washed with phosphate-buffered saline and lysed in 60 mM Tris-HCl, pH 8.5, containing 0.05% Triton® X-100. Cell-associated urokinase-type plasminogen activator (uPA) activity is measured as described by Presta, et al., cited above, using the plasmin chromogenic substrate D-norleucyl-hexahydrotyrosyllysine p-nitroanilide acetate (American Diagnostics, Greenwich, Conn.). Cell-associated protein concentrations are determined using Coomassie blue binding to protein. The results are plotted in FIG. 5. Both FGF-2LI and FGF-2LA exhibit significantly reduced capabilities to induce urokinase-type plasminogen activator.

In vitro anglogenesis evaluations are made by observing whether the mutants induce capillary-like structures in ABAE cells cultured on a 3-dimensional collagen gel. Three-dimensional collagen gel plates (24-well) are prepared by adding 0.5 ml chilled solution of 0.7 mg/ml rat-tail type I collagen (Becton Dickinson Labwares, Bedford, Mass.) containing DMEM and adjusting to neutral pH with $NaHCO_3$ to each well. After formation of collagen gel (about 1–2 mm thickness), ABAE cells are seeded at 50,000 cells/well. The cultures are maintained at 37° C. in DMEM containing 10% calf serum (Hyclone, Logan, Utah) supplemented with penicillin (100 units/ml), streptomycin (100 μg/ml) and L-glutamine (2 mM) until the cultures reach confluency, usually in 5 days by which time the cells form a monolayer on the gel. The medium is then replaced with fresh medium containing different concentrations of FGF-2 or mutants. The cultures are maintained at 37° C. for 48 hours, then discontinued by fixation with cold methanol (−20° C).

Figure 6:
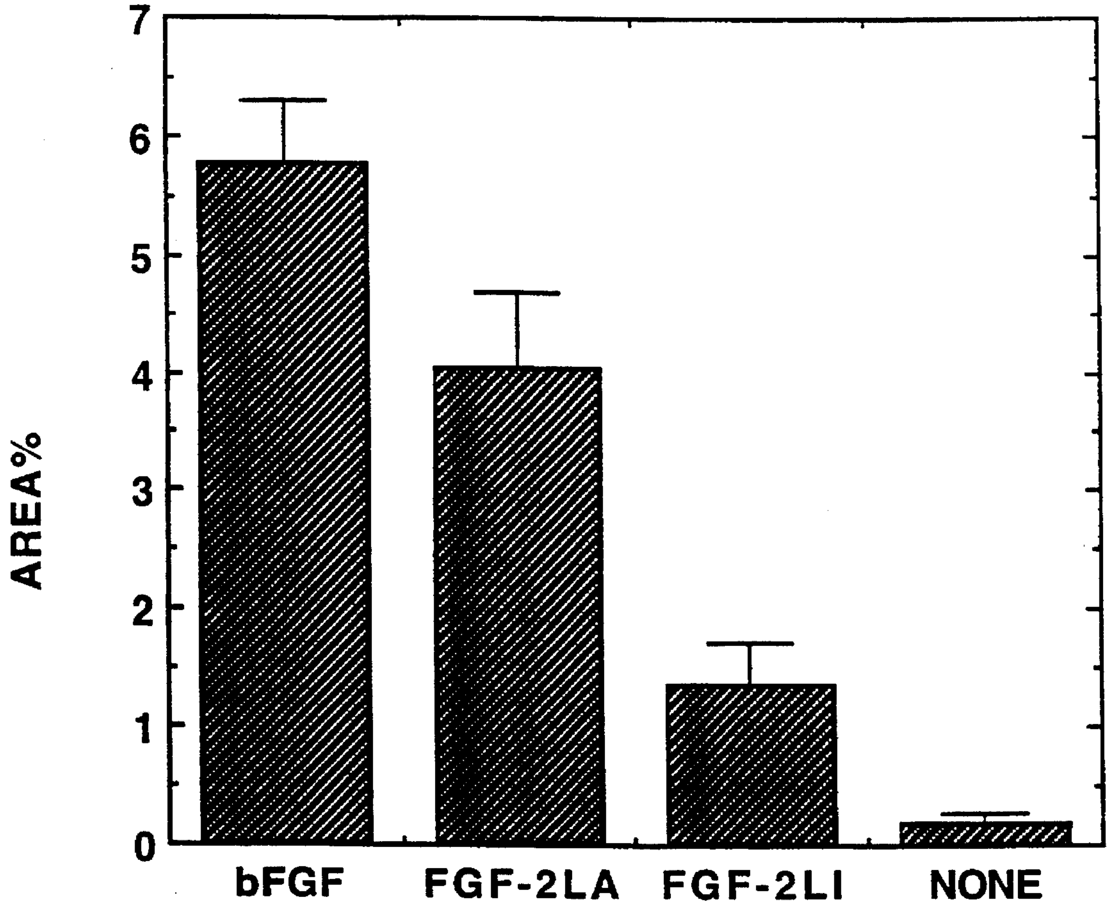
FIG. 6 is a bar graph illustrating the potency of in vitro angiogenic activities of wild-type or mutant FGF-2 (10 ng/ml) as measured by their abilities to induce formation of tube-like structures by ABAE cells cultured on a type I collagen gel. The data are from a typical experiment in which cell cultures of identical conditions are maintained in duplicate wells. Three to four areas of each well are examined by image analysis and the mean value and standard deviation are presented.

The abundance of the capillary-like structures formed by ABAE cells is analyzed by using a Kontron IBAS Image Analyzer assisted with a Hamamatsu C2400 video camera and a Zeiss Axioshop microscope. The phase-contrase image of each field obtained with a video camera is converted to a binary image in which the areas occupied by a capillary-like structure is white and the rest is a black background. The extent of in vitro angiogenesis is then measured as a percentage of the white areas. Cell cultures of identical conditions are maintained in duplicate wells. Three to four areas of each well are examined by image analysis and the mean value and standard deviation are determined. The results from this computer-assisted quantitation method are set out in FIG. 6. The induction of tube formation by mutant FGF-2LI is much less than that by wild-type FGF-2, whereas that by FGF- 2LA is comparable with the wildtype.

In an in vivo model of angiogenesis, FGF-2LI is evaluated using the rabbit ear chamber system modified and improved by Howden, G. F., and Silver, I. A., (*Int. Endodontic J.* 13: 3–16 (1980)), observing the growth factor-induced neovascularization, or its inhibition, by modified growth factors or other reagents.

Rabbits are sedated using 50–70 mg/kg ketamine and 10 mg/kg xylozine administered intramuscularly. The ears are shaved with an electric hair clipper and cleaned with water, followed by Betadine®. To minimize the risk of infection, the rabbits are given 20,000 units/kg benzathine penicillin intramuscularly prior to insertion of the ear chambers. The chamber is inserted into an approximately 0.75 cm area which is not crossed by any major vessels. During the course of the experiments, observations or any minor handling of ear chambers of the animals is done by sedating the animal using the intramuscular administration of a combination of Butorphanol® and acepromazine at levels of 1 mg/kg each. FGF-2 or FGF-2LI bound to heparin-Sepharose® beads in a controlled-release alginate capsule is contained in one of the ear chambers and the other is used as a control containing only the heparin-Sepharose® alginate capsule vehicle. Thus, the effect of the growth factors and the controlled-release capsule alone can be observed simultaneously in the same animal. FGF-2 and FGF-2LI are tested at 1, 10, and 100 ng/chamber in triplicate. The animals are kept for 4 to 6 weeks and neovascularization is observed visually and recorded photographically at weekly intervals.

The criteria for evaluation of the degree of neovascularization using this procedure is set out below.

Criteria for Evaluation of the Degree of Neovascularization

| Observation | Score |
|---|---|
| No Vascularization | 0 |
| Small Buds | 0.5 |
| Extensive Buds | 1.0 |
| Capillary Network Extending to ¼ of the Chamber | 2.0 |
| Capillary Network Extending > ¼ of the Chamber; No Anastomoses | 3.0 |
| Anastomoses from Opposite Sides of the Chamber | 4.0 |
| Extensive Anastomosing Capillary Network Filling Chamber Area | 5.0 |

Figure 8:
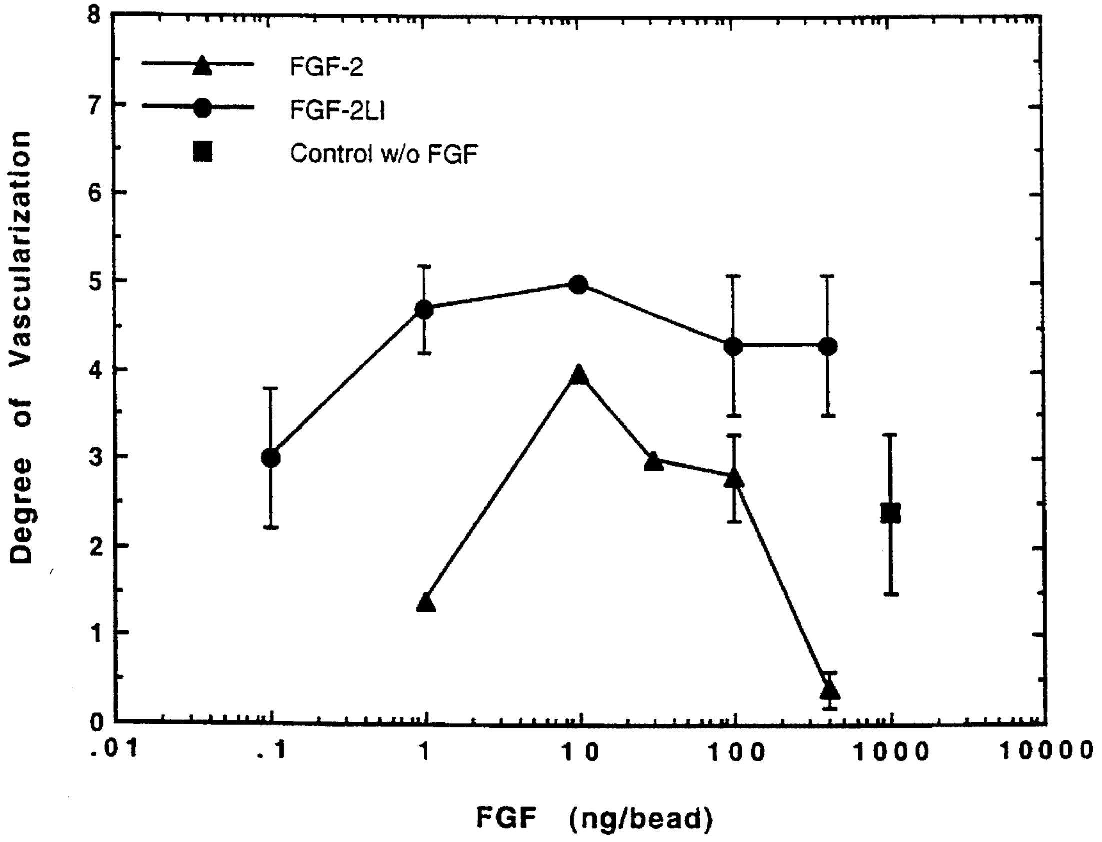
FIG. 8 shows a comparison of the degree of neovascularization induced in a rabbit ear chamber model by FGF-2 (closed triangles) and FGF-2LA (closed circles). A control without FGF is represented by closed squares.

The data, plotted in FIG. 9, show that FGF-2LI is superior to FGF-2 in its potential to induce angiogenesis. Both FGF-2 and FGF-2LI stimulate large vessel formation, their growth across the chamber, resulting in anastomosing vessels with an active blood flow. In comparison, in control chambers that contain alginate-heparin Sepharose® beads, void of exogeneously added growth factors, only short capillaries are formed. The difference in the activity of FGF-2LI compared to FGF-2 is both quantitative and qualitative. Striking stimulatory activity of FGF-2LI compared to FGF-2 is observed over a wide range of concentrations (i.e., from 0.1–400 ng/chamber), and the stimulation is prolific and sustained beyond the time when the stimulatory effect of FGF-2 has subsided. (See FIG. 8.)

Though FGF-2 shows a dose-dependent induction of new blood vessels compared to the vehicle alone, a comparable activity for FGF-2 is observed only at concentrations of 10–100 ng/chamber; at higher dosages, a diminshed response is observed. Interestingly, at 400 ng/chamber of FGF-2, angiogenesis is completely inhibited, while FGF-2LI at the same dose greatly stimulates formation of capillaries and larger vessels. Thus, there is an observed difference in the biological activity of FGF-2LI compared to FGF-2.

Although the in vitro data suggest a reduced angiogenic activity for FGF-2LI, the in vivo studies indicate a superagonist-like behavior. While not meaning to be bound to any theory, it seems that the in vitro assays emphasize a particular property of the loop analogues in an isolated system using a single cell type, whereas the in vivo model provides a contextual environment to observe the largely unknown complex interplay of FGF and other factors in the formation of new blood vessels.

The unexpected discrepancies between the in vitro and in vivo properties of FGF-2LI indicate that the growth factor biological activities are pharmacologically dissociated in some loop analogue embodiments.

EXAMPLE 6

Binding of FGF proteins to different FGF receptors are determined in this example, by measuring the degree of competition for binding to different types of FGF-receptor proteins between a radioiodinated FGF protein and various unlabelled proteins, or by the direct binding of radioiodinated FGF's to various receptor proteins. Binding studies are confirmed by chemical cross-linking of the radioiodinated FGF to soluble receptors in the presence and absence of excess unlabelled FGF.

Sodium heparin from porcine intestinal mucosa (PM-heparin) is obtained from Hepar Industries (Franklin, Ohio). KGF is obtained from UBI (Lake Placid, N.Y.). $Na^{125}I$ is purchased from Amersham (Buckinghamshire, England). FGFs are iodinated using chloramine T. Specific activities of the preparations are $1.2–1.7\times10^5$ cpm/ng FGF and are kept for up to 3 weeks at −70° C. DMEM (1 g glucose/L), calf serum, fetal calf serum (FCS), penicillin, and streptomycin are obtained from Cellgro (Mediatech, Inc., Herndon, Va.). Saline containing 0.05% trypsin, 0.01M sodium phosphate, and 0.02% EDTA (STV) is obtained from Cellgro. Tissue culture dishes are from Falcon Labware Division, Becton Dickinson (Oxnard, Calif.). Four-well tissue culture plates are from Nunc (Rosklide, Denmark).

Soluble FGF receptor proteins are constructed by cloning of the extracellular region of murine FGF receptor 1 (FGFR-1; flg), FGF receptor 2 (FGFR-2; bek) or the KGF receptor (FGFR(IIIb); K-sam) into the alkaline phosphatase-tag expression vector, which encodes for a secreted form of placental alkaline phosphatase (AP). The FGF receptor alkaline phosphatase (FRAP) plasmids are cotransfected into NIH 3T3 cells by electroporation with a selectable neomycin resistance gene. Clonies are selected in G418 (600 μg/ml) and screened for secreted AP enzyme activity in the conditioned medium. Clones of each receptor which produced a high level of AP activity (2 to 4 $A_{405}$ units/min/ml) are then used to produce conditioned medium for binding assays.

Components of the soluble receptor binding reaction mixture include FRAP-conditioned medium (0.24 OD units/min), 2 ng/ml$^{125}$I-FGFs and 200 ng/ml heparin. The FGF-:heparin:FRAP terniary complex is immunoprecipitated with 20 μl of a 1:1 slurry of anti-AP monoclonal antibodies coupled to protein A Sepharose®. All components are mixed at room temperature. The total volume is adjusted to 200 μl by addition of DMEM containing 0.1% bovine serum albumin. Binding is allowed to proceed for 1 to 2 hours at 24° C., after which time bound receptor complex or the ligand is recovered by centrifugation at 4° C. (10 s at 2,000×g). The pelleted material is washed twice with 500 μl of an ice cold buffer containing HEPES (20 mM), NaCl (150 mM), glycerol (10%) and Triton® X-100 (1%). $^{125}$I-FGF binding is quantitated by counting of the samples in a gamma counter (LKB). Alternatively, AP enzyme activity of the FRAP protein is determined by transferring the FRAP receptor bound to heparin-Sepharose® to a flat-bottom microtiter plate in a volume of 50 μl of PBS. The reaction is initiated by addition of substrate (50 μl of 2× solution of AP assay buffer containing 2M diethanoiamine, 1 mM $MgCl_2$, 20 mM homoarginine and 12 mM p-nitrophenyl phosphate). The reaction is followed at room temperature at 405 nm in a kinetic microplate reader.

Receptor binding is determined by quantitating release of labelled FGF from receptors. Briefly, FGF bound to heparan sulfate low affnity sites is released from the cell surface by a 5 minute incubation with an ice cold solution containing 1.6M Nacl, 20 mM HEPES, pH 7.4, and the amount of radioactivity release determined in a gamma-counter. FGF bound to high affinity receptors is dissociated by a 2M NaCl (20 mM acetate buffer, pH 4.0) extraction, and the released labelled FGF is quantitated.

Chemical cross-linking experiments are carried out at room temperature in a volume of 20 μl in siliconized 0.5-ml microcentrifuge tubes. The reaction mixtures contain FGF receptor immobilized to anti-AP monoclonal antibodies coupled to protein A Sepharose®, 200 ng/ml heparin, 2 ng/ml$^{125}$I-bFGF, 20 mM phosphate buffer (pH 7.4), and 140 mM NaCl. After a 90 minute incubation, 1 ml of a solution of disuccinimidyl suberate (Pierce) dissolved in dimethyl sulfoxide is added to give a final concentration of 0.15 mM, and the mixture incubated for an additional 30 minutes. The reaction is quenched by addition of 1 ml of 200 mM ethanolamine-HCl (pH 8.0) for 30 min. The reaction mixtures are diluted 1:1 with 2× SDS-polyacrylamide gel electrophoresis loading buffer and electrophoresed on an SDS-12% polyacrylamide gel. Cross-linked FGF to the FGF receptor are detected by autoradiography on Kodak XAR film.

Figure 9A:
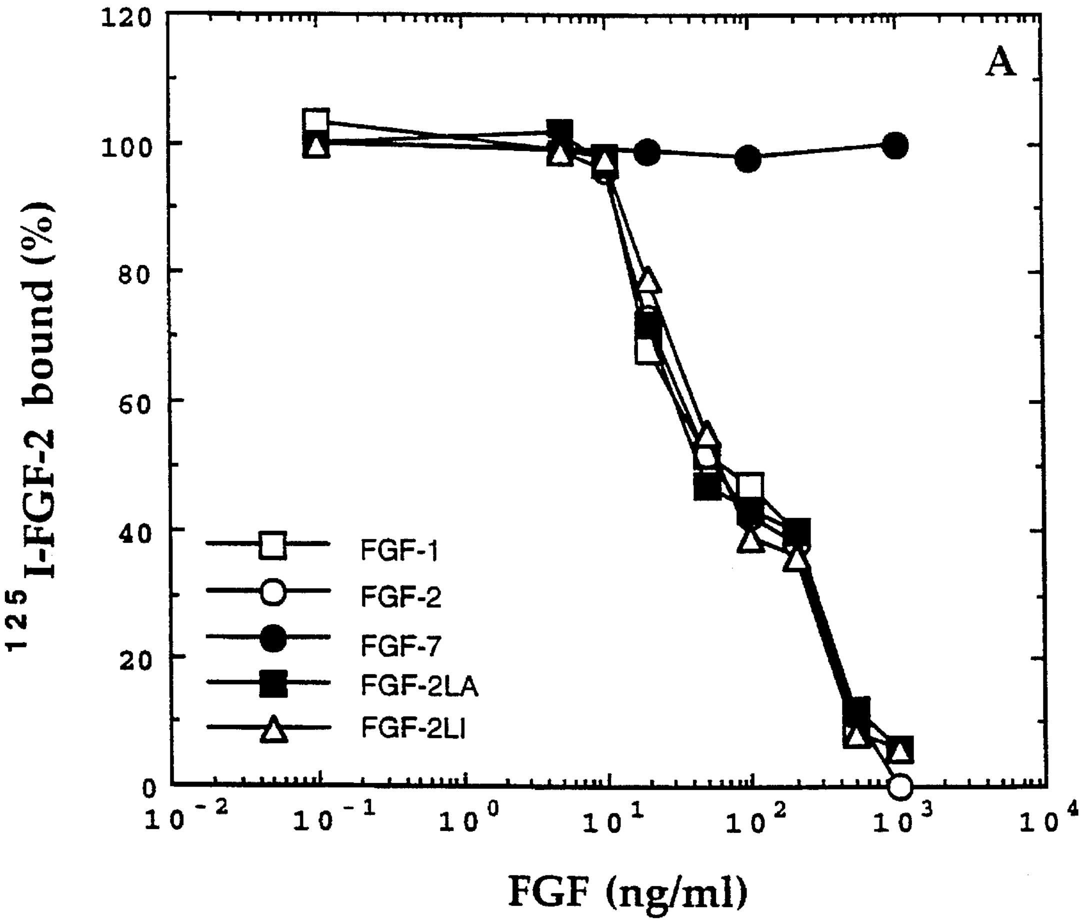
FIG. 9A plots the binding of $^{125}$I-FGF-2 as a function of added FGF-1 (open circles), FGF-2 (open squares), FGF-7 (closed circles), FGF-2LA (closed squares), and FGF-2LI (open triangles) to soluble recombinant FGF-receptor type 1 as a function of added unlabelled FGF proteins.
Figure 9B:
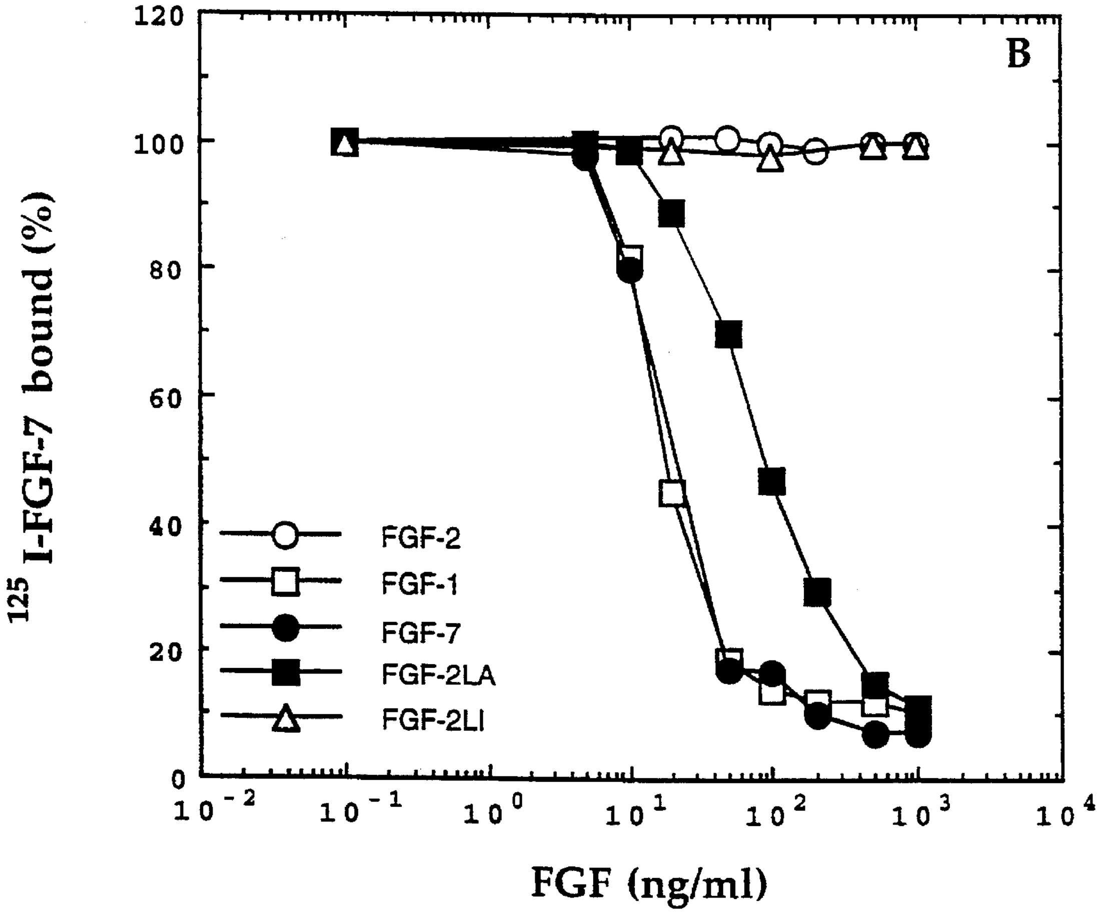
FIG. 9B plots a similar binding profile, except that soluble recombinant FGF-2(IIIc) is employed.

The position of the surface loop in FGF-2 coincides with a variable sequence region in the FGF family of proteins where various insertions occur. Since this region may be involved with determining ligand-receptor binding specificity the binding profiles of the loop mutants, LA and LI, to FGFR1 (Flg) and FGFR2 sub-type IIIb (FGF-7 or KGF receptor), which does not bind FGF-2 are determined. FIGS. 9A and 9B show the competition binding curves to soluble versions of FGFR1 and FGFR2(IIIb) for FGF-1, FGF-2, FGF-7 and the loop mutants following the displacement of radioiodinated FGF-2 and FGF-7 from the soluble receptor, respectively. FGF-1, FGF-2, FGF-2LA and FGF-2LI bind equally well to FGFR1, but no binding of FGF-7 is detected (FIG. 9A).

The binding profiles for the binding of various FGF proteins to FGFR2(IIIb) (FIG. 9B) show that FGF-7 and FGF-1 bind with the same affinity and that FGF-2 and the FGF-2L1 mutant do not bind to this receptor type; however, the binding of the LA mutant to FGFR2(IIIb) is only about 5-times less than that of FGF-7 or FGF-1. That the binding profile of FGF-2LA now mirrors that for FGF-1 and not of FGF-2, the FGF-1 loop-host protein, is consistent with the involvement of this surface loop in determining receptor-ligand specificity.

The binding specificities of radiolabelled FGF proteins and loop mutants to various soluble FGF receptors are confirmed by chemical cross-linking of the factors to the receptors in the presence and absence of an excess of the unlabelled FGF. FGF-1, FGF-2, FGF-2LA and FGF-2LI bind to FGFR1, and addition of an excess of the unlabelled FGF abolished cross-linking of $^{125}$I-FGF. Cross-linking of $^{125}$I-FGF-7 to FGFR1 is not detected. An identical cross-linking profile is obtained when the binding experiments are repeated using a soluble FGFR2 receptor. The cross-linking profile for FGFR2(IIIb) reveal that only FGF-1, FGF-7 and FGF-2LA bind to this receptor and that FGF-2 and the FGF-2LI mutant are excluded from binding. The cross-linking studies are consistent with the binding data presented in FIGS. 2, 3, and 8.

EXAMPLE 7

The FGF-7 loop sequence is introduced into FGF-2, and the properties of the new FGF-2 loop mutant are observed in this example.

A FGF-2 loop mutant denoted FGF-2LK containing the corresponding 9-residue loop sequence Ala-Lys-Trp-Thr-His-Asn-Gly-Gly-Glu from FGF-7 (residues 154–162 of SEQ ID NO 8) is constructed using the procedures outlined in Examples 1 and 2 above.

FGF-2LK shows an apparent decrease in affinity for heparin. NaCl elution from heparin-Sepharose® is about 0.7M NaCl, compared with 1.4M NaCl for the wild-type protein. The molarity of NaCl required to elute the LK mutant is similar to that required to elute FGF-7. The lowered affinity of the FGF-2LK mutant for heparin suggests that the loop sequence, although not directly involved in binding to heparin, is able to modify the affinity of the protein for heparin.

In receptor binding experiments like those set out in Example 6 above, the FGF-2LK protein is unable to displace or compete with the binding of $^{125}$I-FGF-2 to FGF receptor type 1, but is able to compete with binding of $^{125}$I-FGF-7 to FGF receptor type 2 (IIIb), whereas FGF-2 does not compete with binding. Although the potency of the FGF-2LK is about 100 times weaker than the competition observed using unlabelled FGF-7, a clear change in receptor-ligand binding profiles is observed.

The results indicate that the loop sequence from FGF-7 confers receptor-ligand specificity, and allows for the binding of the FGF-2LK mutant to a receptor subtype that binds FGF-7 but not FGF-2. Conversely, the loop sequence from FGF-7 in the FGF-2 host molecule abolishes binding of the protein to FGF receptor 1. That the affinity of the interaction is decreased by a factor of 100 suggests that other determinants in FGF-7 are involved in contributing to the binding affinity of the ligand to the receptor. The evidence also suggests that the loop sequences may modify binding to heparin.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention as defined in the appended claims.

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 21
( B ) TYPE: amino acid
( C ) STRANDEDNESS: single
( D ) TOPOLOGY: linear ( i i ) MOLECULE TYPE:
( A ) DESCRIPTION: peptide ( v ) FRAGMENT TYPE: internal fragment ( i x ) FEATURE:
( A ) NAME/KEY: fibroblast growth factor-2 loop region ( x ) PUBLICATION INFORMATION:
( A ) AUTHORS: Eriksson, A.E., et al.
( B ) TITLE: Three-dimensional structure of human basic fibroblast growth factor
( C ) JOURNAL: Proc. Nat. Acad. Sci. USA
( D ) VOLUME: 88
( F ) PAGES: 3441-3445; sequence on page 3444
( G ) DATE: April 1991
( K ) RELEVANT RESIDUES IN SEQ ID NO: segment corresponding to polypeptide residues 110 to 130

( x i ) SEQUENCE DESCRIPTION: SEQ ID NO:1:

```
Asn Asn Tyr Asn Thr Tyr Arg Ser Arg Lys Tyr Thr Ser Trp Tyr
110                 115                 120

Val Ala Leu Lys Arg Thr
125                 130
```

( 2 ) INFORMATION FOR SEQ ID NO:2:

( i ) SEQUENCE CHARACTERISTICS:
( A ) LENGTH: 23
( B ) TYPE: amino acid
( C ) STRANDEDNESS: single
( D ) TOPOLOGY: linear ( i i ) MOLECULE TYPE:
( A ) DESCRIPTION: peptide ( v ) FRAGMENT TYPE: internal fragment ( i x ) FEATURE:
( A ) NAME/KEY: bovine and human fibroblast growth factor-1 loop region
( D ) OTHER INFORMATION: residue 121 is Asn in the human sequence and His in the bovine sequence ( x ) PUBLICATION INFORMATION:
( A ) AUTHORS: Eriksson, A.E., et al.
( B ) TITLE: Three-dimensional structure of human basic fibroblast growth factor
( C ) JOURNAL: Proc. Nat. Acad. Sci. USA
( D ) VOLUME: 88
( F ) PAGES: 3441-3445; sequence on page 3444
( G ) DATE: April 1991
( K ) RELEVANT RESIDUES IN SEQ ID NO: segment corresponding to polypeptide residues 107 to 129 of bovine sequence ( x i ) SEQUENCE DESCRIPTION: SEQ ID NO:2:

```
Asn His Tyr Asn Thr Tyr Ile Ser Lys Lys His Ala Glu Lys Xaa
```

-continued 110 115 120

Trp Phe Val Gly Leu Lys Lys Asn
125

( 2 ) INFORMATION FOR SEQ ID NO:3:

( i ) SEQUENCE CHARACTERISTICS:
( A ) LENGTH: 21
( B ) TYPE: amino acid
( C ) STRANDEDNESS: single
( D ) TOPOLOGY: linear ( i i ) MOLECULE TYPE:
( A ) DESCRIPTION: peptide ( v ) FRAGMENT TYPE: internal fragment ( i x ) FEATURE:
( A ) NAME/KEY: interleukin-1a loop region ( x ) PUBLICATION INFORMATION:
( A ) AUTHORS: Eriksson, A.E., et al.
( B ) TITLE: Three-dimensional structure of human basic fibroblast growth factor
( C ) JOURNAL: Proc. Nat. Acad. Sci. USA
( D ) VOLUME: 88
( F ) PAGES: 3441-3445; sequence on page 3444
( G ) DATE: April 1991
( K ) RELEVANT RESIDUES IN SEQ ID NO: segment corresponding to polypeptide residues 223 to 243

( x i ) SEQUENCE DESCRIPTION: SEQ ID NO:3:

Asn Asn Lys Leu Glu Phe Glu Ser Ala Gln Phe Pro Asn Trp Tyr
225 230 235

Ile Ser Thr Ser Glu Ala
240

( 2 ) INFORMATION FOR SEQ ID NO:4:

( i ) SEQUENCE CHARACTERISTICS:
( A ) LENGTH: 37
( B ) TYPE: amino acid
( C ) STRANDEDNESS: single
( D ) TOPOLOGY: linear ( i i ) MOLECULE TYPE:
( A ) DESCRIPTION: peptide ( v ) FRAGMENT TYPE: internal fragment ( i x ) FEATURE:
( A ) NAME/KEY: fibroblast growth factor-3 loop region ( x ) PUBLICATION INFORMATION:
( A ) AUTHORS: Miyamoto, M., et al.
( B ) TITLE: Molecular cloning of a Novel Cytokine cDNA Encoding the Ninth Member of the Fibroblast Growth Factor Family
( C ) JOURNAL: Molecular and Cellular Biology
( D ) VOLUME: 13
( E ) ISSUE: 7
( F ) PAGES: 4251-4259; Figure 2 on page 4254
( G ) DATE: July 1993
( K ) RELEVANT RESIDUES IN SEQ ID NO: segment corresponding to polypeptide residues 124 to 160

( x i ) SEQUENCE DESCRIPTION: SEQ ID NO:4:

Leu Gly Tyr Asn Thr Tyr Ala Ser Arg Leu Tyr Arg Thr Val Ser
125 130 135

Ser Thr Pro Gly Ala Arg Arg Gln Pro Ser Ala Glu Arg Leu Trp
140 145 150

Tyr Val Ser Val Asn Gly Lys

-continued 155 160

( 2 ) INFORMATION FOR SEQ ID NO:5:

( i ) SEQUENCE CHARACTERISTICS:
( A ) LENGTH: 21
( B ) TYPE: amino acid
( C ) STRANDEDNESS: single
( D ) TOPOLOGY: linear ( i i ) MOLECULE TYPE:
( A ) DESCRIPTION: peptide ( v ) FRAGMENT TYPE: internal fragment ( i x ) FEATURE:
( A ) NAME/KEY: fibroblast growth factor-4 loop region ( x ) PUBLICATION INFORMATION:
( A ) AUTHORS: Burgess, W.H., and Maciag, T.
( B ) TITLE: The Heparin-Binding (Fibroblast) Growth Factor Family of Proteins
( C ) JOURNAL: Ann. Rev. Biochem.
( D ) VOLUME: 58
( F ) PAGES: 575-606, Figure 1 on page 580
( G ) DATE: 1989
( K ) RELEVANT RESIDUES IN SEQ ID NO: segment corresponding to polypeptide residues 164 to 184

( x i ) SEQUENCE DESCRIPTION: SEQ ID NO:5:

Asn Asn Tyr Asn Ala Tyr Glu Ser Tyr Lys Tyr Pro Gly Met Phe
165 170 175

Ile Ala Leu Ser Lys Asn
180

( 2 ) INFORMATION FOR SEQ ID NO:6:

( i ) SEQUENCE CHARACTERISTICS:
( A ) LENGTH: 27
( B ) TYPE: amino acid
( C ) STRANDEDNESS: single
( D ) TOPOLOGY: linear ( i i ) MOLECULE TYPE:
( A ) DESCRIPTION: peptide ( v ) FRAGMENT TYPE: internal fragment ( i x ) FEATURE:
( A ) NAME/KEY: fibroblast growth factor-5 loop region ( x ) PUBLICATION INFORMATION:
( A ) AUTHORS: Burgess, W.H., and Maciag, T.
( B ) TITLE: The Heparin-Binding (Fibroblast) Growth Factor Family of Proteins
( C ) JOURNAL: Ann. Rev. Biochem.
( D ) VOLUME: 58
( F ) PAGES: 575-606, Figure 1 on page 580
( G ) DATE: 1989
( K ) RELEVANT RESIDUES IN SEQ ID NO: segment corresponding to polypeptide residues 168 to 194

( x i ) SEQUENCE DESCRIPTION: SEQ ID NO:6:

Asn Ser Tyr Asn Thr Tyr Ala Ser Ala Ile His Arg Thr Glu Lys
170 175 180

Thr Gly Arg Glu Trp Tyr Val Ala Leu Asn Lys Arg
185 190

( 2 ) INFORMATION FOR SEQ ID NO:7:

( i ) SEQUENCE CHARACTERISTICS:
( A ) LENGTH: 21 residues
( B ) TYPE: amino acid ( C ) STRANDEDNESS: single
( D ) TOPOLOGY: linear ( i i ) MOLECULE TYPE:
( A ) DESCRIPTION: peptide ( v ) FRAGMENT TYPE: internal fragment ( i x ) FEATURE:
( A ) NAME/KEY: fibroblast growth factor-6 loop region ( x ) PUBLICATION INFORMATION:
( A ) AUTHORS: Miyamoto, M., et al.
( B ) TITLE: Molecular cloning of a Novel Cytokine cDNA Encoding the Ninth Member of the Fibroblast Growth Factor Family
( C ) JOURNAL: Molecular and Cellular Biology
( D ) VOLUME: 13
( E ) ISSUE: 7
( F ) PAGES: 4251-4259; Figure 2 on page 4254
( G ) DATE: July 1993
( K ) RELEVANT RESIDUES IN SEQ ID NO: segment corresponding to polypeptide residues 166 to 186

( x i ) SEQUENCE DESCRIPTION: SEQ ID NO:7:

```
Asn Asn Tyr Asn Ala Tyr Glu Ser Asp Leu Tyr Gln Gly Thr Tyr
                170                 175                 180

Ile Ala Leu Ser Lys Tyr
                185
```

( 2 ) INFORMATION FOR SEQ ID NO:8:

( i ) SEQUENCE CHARACTERISTICS:
( A ) LENGTH: 25 residues
( B ) TYPE: amino acid
( C ) STRANDEDNESS: single
( D ) TOPOLOGY: linear ( i i ) MOLECULE TYPE:
( A ) DESCRIPTION: peptide ( v ) FRAGMENT TYPE: internal fragment ( i x ) FEATURE:
( A ) NAME/KEY: fibroblast growth factor-7 loop region ( x ) PUBLICATION INFORMATION:
( A ) AUTHORS: Miyamoto, M., et al.
( B ) TITLE: Molecular cloning of a Novel Cytokine cDNA Encoding the Ninth Member of the Fibroblast Growth Factor Family
( C ) JOURNAL: Molecular and Cellular Biology
( D ) VOLUME: 13
( E ) ISSUE: 7
( F ) PAGES: 4251-4259; Figure 2 on page 4254
( G ) DATE: July 1993
( K ) RELEVANT RESIDUES IN SEQ ID NO: segment corresponding to polypeptide residues 146 to 170

( x i ) SEQUENCE DESCRIPTION: SEQ ID NO:8:

```
Asn His Tyr Asn Thr Tyr Ala Ser Ala Lys Trp Thr His Asn Gly
                150                 155                 160

Gly Glu Met Phe Val Ala Leu Asn Gln Lys
                16
```

( 2 ) INFORMATION FOR SEQ ID NO:9:

( i ) SEQUENCE CHARACTERISTICS:
( A ) LENGTH: 21 residues
( B ) TYPE: amino acid
( C ) STRANDEDNESS: single
( D ) TOPOLOGY: linear ( i i ) MOLECULE TYPE:

-continued ( A ) DESCRIPTION: peptide ( v ) FRAGMENT TYPE: internal fragment ( i x ) FEATURE:
( A ) NAME/KEY: fibroblast growth factor-8 loop region ( x ) PUBLICATION INFORMATION:
( A ) AUTHORS: Tanaka, A., et al.
( B ) TITLE: Cloning and Characterization of an Antrogen- Induced Growth Factor
( C ) JOURNAL: Proc. Natl. Acad. Sci. USA
( D ) VOLUME: 89
( F ) PAGES: 8928-8931; Figure 2 on page 8930
( G ) DATE: October 1992
( K ) RELEVANT RESIDUES IN SEQ ID NO: segment corresponding to polypeptide residues 136 to 156

( x i ) SEQUENCE DESCRIPTION: SEQ ID NO:9:

```
Asn Asn Tyr Thr Ala Leu Gln Asn Ala Lys Tyr Glu Gly Trp Tyr
                140                 145                 150

Met Ala Phe Thr Arg Lys
                155
```

( 2 ) INFORMATION FOR SEQ ID NO:10:

( i ) SEQUENCE CHARACTERISTICS:
( A ) LENGTH: 27 residues
( B ) TYPE: amino acid
( C ) STRANDEDNESS: single
( D ) TOPOLOGY: linear ( i i ) MOLECULE TYPE:
( A ) DESCRIPTION: peptide ( v ) FRAGMENT TYPE: internal fragment ( i x ) FEATURE:
( A ) NAME/KEY: fibroblast growth factor-9 loop region ( x ) PUBLICATION INFORMATION:
( A ) AUTHORS: Miyamoto, M., et al.
( B ) TITLE: Molecular cloning of a Novel Cytokine cDNA Encoding the Ninth Member of the Fibroblast Growth Factor Family
( C ) JOURNAL: Molecular and Cellular Biology
( D ) VOLUME: 13
( E ) ISSUE: 7
( F ) PAGES: 4251-4259; Figure 2 on page 4254
( G ) DATE: July 1993
( K ) RELEVANT RESIDUES IN SEQ ID NO: segment corresponding to polypeptide residues 143 to 167

( x i ) SEQUENCE DESCRIPTION: SEQ ID NO:10:

```
Asn Trp Tyr Asn Thr Tyr Ser Ser Asn Leu Tyr Lys His Val Asp
        145                 150                 155

Thr Gly Arg Arg Tyr Tyr Val Ala Leu Asn Lys Asp
        160                 165
```

( 2 ) INFORMATION FOR SEQ ID NO:11:

( i ) SEQUENCE CHARACTERISTICS:
( A ) LENGTH: 74 residues
( B ) TYPE: nucleic acid
( C ) STRANDEDNESS: single
( D ) TOPOLOGY: linear ( i i ) MOLECULE TYPE:
( A ) DESCRIPTION: oligonucleotide ( v ) FRAGMENT TYPE: synthetic DNA ( i x ) FEATURE:
( D ) OTHER INFORMATION: used in pre- -continued paring constructs ( x i ) SEQUENCE DESCRIPTION: SEQ ID NO:11:

CGAACGATTG GAATCTAATA ACTACAATAC GTACCGGTCT GCGCAGTTTC 50

CTAACTGGTA TGTGGCACTT AAGC 74

( 2 ) INFORMATION FOR SEQ ID NO:12:

( i ) SEQUENCE CHARACTERISTICS:
( A ) LENGTH: 76 residues
( B ) TYPE: nucleic acid
( C ) STRANDEDNESS: single
( D ) TOPOLOGY: linear ( i i ) MOLECULE TYPE:
( A ) DESCRIPTION: oligonucleotide ( v ) FRAGMENT TYPE: synthetic DNA ( i x ) FEATURE:
( D ) OTHER INFORMATION: used in preparing constructs ( x i ) SEQUENCE DESCRIPTION: SEQ ID NO:12:

GTACGCTTAA GTGCCACATA CCAGTTAGGA AACTGCGCAG ACCGGTACGT 50

ATTGTAGTTA TTAGATTCCA ATCGTT 76

( 2 ) INFORMATION FOR SEQ ID NO:13:

( i ) SEQUENCE CHARACTERISTICS:
( A ) LENGTH: 80 residues
( B ) TYPE: nucleic acid
( C ) STRANDEDNESS: single
( D ) TOPOLOGY: linear ( i i ) MOLECULE TYPE:
( A ) DESCRIPTION: oligonucleotide ( v ) FRAGMENT TYPE: synthetic DNA ( i x ) FEATURE:
( D ) OTHER INFORMATION: used in preparing constructs ( x i ) SEQUENCE DESCRIPTION: SEQ ID NO:13:

CGAACGATTG GAATCTAATA ACTACAATAC GTACCGGTCT AAAAAGCATG 50

CTGAAAAACA CTGGTATGTG GCACTTAAGC 80

( 2 ) INFORMATION FOR SEQ ID NO:14:

( i ) SEQUENCE CHARACTERISTICS:
( A ) LENGTH: 82 residues
( B ) TYPE: nucleic acid
( C ) STRANDEDNESS: single
( D ) TOPOLOGY: linear ( i i ) MOLECULE TYPE:
( A ) DESCRIPTION: oligonucleotide ( v ) FRAGMENT TYPE: synthetic DNA ( i x ) FEATURE:
( D ) OTHER INFORMATION: used in preparing constructs ( x i ) SEQUENCE DESCRIPTION: SEQ ID NO:14:

GTACGCTTAA GTGCCACATA CCAGTGTTTT TCAGCATGCT TTTTAGACCG 50

GTACGTATTG TAGTTATTAG ATTCCAATCG TT 82

-continued ( 2 ) INFORMATION FOR SEQ ID NO:15:

( i ) SEQUENCE CHARACTERISTICS:
( A ) LENGTH: 471 bases
( B ) TYPE: nucleic acid
( C ) STRANDEDNESS: single
( D ) TOPOLOGY: linear ( i i ) MOLECULE TYPE:
( A ) DESCRIPTION: DNA encoding a protein ( v ) FRAGMENT TYPE: entire sequence ( v i ) IMMEDIATE SOURCE: constructed ( i x ) FEATURE:
( D ) OTHER INFORMATION: FGF-2 having surface loop residues 118 to 122 replaced with corresponding structural elements from interleukin-1a ( x i ) SEQUENCE DESCRIPTION: SEQ ID NO:15:

```
ATG GCT GAA GGG GAA ATC ACC ACG CTG CCC GCC CTT CCG GAG GAT   45
Met Ala Glu Gly Glu Ile Thr Thr Leu Pro Ala Leu Pro Glu Asp
                  5                  10                  15

GGC GGC AGC GGC GCC TTC CCG CCC GGG CAC TTC AAG GAC CCC AAG   90
Gly Gly Ser Gly Ala Phe Pro Pro Gly His Phe Lys Asp Pro Lys
                 20                  25                  30

CGG CTG TAC TGC AAA AAC GGG GGC TTC TTC CTG CGC ATC CAC CCC  135
Arg Leu Tyr Cys Lys Asn Gly Gly Phe Phe Leu Arg Ile His Pro
                 35                  40                  45

GAC GGC CGA GTT GAC GGG GTC CGG GAG AAG AGC GAC CCT CAC ATC  180
Asp Gly Arg Val Asp Gly Val Arg Glu Lys Ser Asp Pro His Ile
                 50                  55                  60

AAG CTA CAA CTT CAA GCA GAA GAG AGA GGA GTT GTG TCT ATC AAA  225
Lys Leu Gln Leu Gln Ala Glu Glu Arg Gly Val Val Ser Ile Lys
                 65                  70                  75

GGA GTG TGT GCT AAC CGG TAC CTG GCT ATG AAG GAA GAT GGA AGA  270
Gly Val Cys Ala Asn Arg Tyr Leu Ala Met Lys Glu Asp Gly Arg
                 80                  85                  90

TTA CTG GCT TCT AAA TGT GTT ACG GAT GAG TGT TTC TTT TTT GAA  315
Leu Leu Ala Ser Lys Cys Val Thr Asp Glu Cys Phe Phe Phe Glu
                 95                 100                 105

CGA TTG GAA TCT AAT AAC TAC AAT ACT TAC CGG TCT GCG CAG TTT  360
Arg Leu Glu Ser Asn Asn Tyr Asn Thr Tyr Arg Ser Ala Gln Phe
                110                 115                 120

CCT AAC TGG TAT GTG GCA TTG AAA CGA ACT GGG CAG TAT AAA CTT  405
Pro Asn Trp Tyr Val Ala Leu Lys Arg Thr Gly Gln Tyr Lys Leu
                125                 130                 135

GGT TCC AAA ACA GGA CCT GGG CAG AAA GCT ATA CTT TTT CTT CCA  450
Gly Ser Lys Thr Gly Pro Gly Gln Lys Ala Ile Leu Phe Leu Pro
                140                 145                 150

ATG TCT GCT AAG AGC TGA TAA                                  471
Met Ser Ala Lys Ser
    155
```

( 2 ) INFORMATION FOR SEQ ID NO:16:

( i ) SEQUENCE CHARACTERISTICS:
( A ) LENGTH: 477 bases
( B ) TYPE: nucleic acid
( C ) STRANDEDNESS: single
( D ) TOPOLOGY: linear ( i i ) MOLECULE TYPE:
( A ) DESCRIPTION: DNA encoding a protein ( v ) FRAGMENT TYPE: entire sequence -continued ( v i ) IMMEDIATE SOURCE: constructed ( i x ) FEATURE:
( D ) OTHER INFORMATION: FGF-2 having surface loop residues 118 to 122 replaced with corresponding structural elements from bovine FGF-1

( x i ) SEQUENCE DESCRIPTION: SEQ ID NO:16:

ATG GCT GAA GGG GAA ATC ACC ACG CTG CCC GCC CTT CCG GAG GAT 45
Met Ala Glu Gly Glu Ile Thr Thr Leu Pro Ala Leu Pro Glu Asp
5 10 15

GGC GGC AGC GGC GCC TTC CCG CCC GGG CAC TTC AAG GAC CCC AAG 90
Gly Gly Ser Gly Ala Phe Pro Pro Gly His Phe Lys Asp Pro Lys
20 25 30

CGG CTG TAC TGC AAA AAC GGG GGC TTC TTC CTG CGC ATC CAC CCC 135
Arg Leu Tyr Cys Lys Asn Gly Gly Phe Phe Leu Arg Ile His Pro
35 40 45

GAC GGC CGA GTT GAC GGG GTC CGG GAG AAG AGC GAC CCT CAC ATC 180
Asp Gly Arg Val Asp Gly Val Arg Glu Lys Ser Asp Pro His Ile
50 55 60

AAG CTA CAA CTT CAA GCA GAA GAG AGA GGA GTT GTG TCT ATC AAA 225
Lys Leu Gln Leu Gln Ala Glu Glu Arg Gly Val Val Ser Ile Lys
65 70 75

GGA GTG TGT GCT AAC CGG TAC CTG GCT ATG AAG GAA GAT GGA AGA 270
Gly Val Cys Ala Asn Arg Tyr Leu Ala Met Lys Glu Asp Gly Arg
80 85 90

TTA CTG GCT TCT AAA TGT GTT ACG GAT GAG TGT TTC TTT TTT GAA 315
Leu Leu Ala Ser Lys Cys Val Thr Asp Glu Cys Phe Phe Phe Glu
95 100 105

CGA TTG GAA TCT AAT AAC TAC AAT ACT TAC CGG TCT AAA AAG CAT 360
Arg Leu Glu Ser Asn Asn Tyr Asn Thr Tyr Arg Ser Lys Lys His
110 115 120

GCT GAA AAA CAC TGG TAT GTG GCA TTG AAA CGA ACT GGG CAG TAT 405
Ala Glu Lys His Trp Tyr Val Ala Leu Lys Arg Thr Gly Gln Tyr
125 130 135

AAA CTT GGT TCC AAA ACA GGA CCT GGG CAG AAA GCT ATA CTT TTT 450
Lys Leu Gly Ser Lys Thr Gly Pro Gly Gln Lys Ala Ile Leu Phe
140 145 150

CTT CCA ATG TCT GCT AAG AGC TGA TAA 477
Leu Pro Met Ser Ala Lys Ser
155

BIBLIOGRAPHY

Arakawa, T. and Fox G. M., Eur. Pat. Ap. Pub. No. 320,148 (1989).

Baird, A., et al., *Proc. Nat. Acad. Sci. U.S.A.* 85: 2324–2328 (1988).

Baird, A., and Böhlen, P., *Handbook of Exp. Pharmacol.* 95(1): 369– 418, Springer, 1990.

Bergonzoni, L., et al., Eur. Pat. Ap. Pub. No. 363,675 (1990).

Davidson, J. M., et al., *J. Cell Bio.* 100: 1219–1227 (1985).

Eriksson, E. A., et al., *Proc. Nat. Acad. Sci. U.S.A.* 88: 3441–3445 (1991).

Feige, J. J. et al., *Proc. Nat. Acad. Sci. U.S.A.* 86: 3174–3178 (1989).

Fiddes, J. C., et al., Eur. Pat. Ap. Pub. No. 298,723 (1989).

Franco, W. P., U.S. Pat. No. 4,378,347, Mar. 29, 1983.

Givol, D., and Yayon, A., *FASEB J.* 6: 3362–3369 (1992).

Gospardarowicz, D., et al., *Proc. Nat. Acad. Sci.* 81: 6963–6967 (1984).

Howden, G. F., and Silver, I. A., *Int. Endodontic J.* 13: 3–6 (1980).

Hynes, T. R., et al., *Nature* 339: 73–76 (1989).

Jaye, M., et al., *Biochim. Biophys. Acta* 1135: 185–199 (1992).

Johnson, D. E., and Williams, L. T., *Adv. Can. Res.* 60: 1–41 (1993).

Miyamoto, M., et al., *Mol. Cell. Biol.* 13: 4251–4259 (1993).

Moscatelli, D., *J. Cell. Physiol.* 131: 123–130 (1987).

Presta, M., et al., *B.B.R.C.* 185: 1098–1107 (1992).

Seddon, A. P. et al., *Annals N.Y. Acad. Sci.* 638: 98–108 (1991).

Seno, M., et al., Eur. Pat. Ap. Pub. Nos. 281,822 (1988) and 326,907 (1989).

Seno, M., et al., *Eur. J. Biochem.* 188: 239–245 (1990).

Tanaka, A., et al., *Proc. Natl. Acad. Sci. U.S.A.* 89: 8928–8932 (1992).

Werner, S., et al., *Mol. Cell. Bio.* 12: 82–88 (1992).

Yayon, A., et al., *EMBO J.* 11: 1885–1890 (1992).

Zhang, J., et al., *Proc. Nat. Acad. Sci. U.S.A.* 88: 3446–3450 (1991).

Zhu, H., et al., *Science* 251: 90–93 (1991).

We claim:

1. An FGF-2 analogue wherein the amino acids corresponding to FGF-2 amino acids 118 to 122 of SEQ ID NO: 1 have been replaced with an amino acid sequence selected from the group consisting of (a) FGF-1 amino acids 112–123 of SEQ ID NO: 2, (b) FGF-1 amino acids 115–121 of SEQ ID NO: 2, (c) FGF-3 amino acids 132–152 of SEQ ID NO: 4, (d) FGF-4 amino acids 172–176 of SEQ ID NO: 5, (e) FGF-5 amino acids 176–186 of SEQ ID NO: 6, (f) FGF-6 amino acids 174–178 of SEQ ID NO: 7, (g) FGF-7 amino acids 154–162 of SEQ ID NO: 8, (h) FGF-8 amino acids 144–148 of SEQ ID NO: 9, (i) FGF-9 amino acids 151–161 of SEQ ID NO: 10, and (j) interleukin-113 amino acids 231–235 of SEQ ID NO: 3 wherein said analogue is capable of binding to heparin.

2. An FGF-2 analogue of claim 1 wherein the amino acids corresponding to FGF-2 amino acids 118–122 of SEQ ID NO: 1 have been replaced with an amino acid sequence selected from the group consisting of (a) FGF-1 amino acids 115–121 of SEQ ID NO: 2, (b) FGF-7 amino acids 154–162 of SEQ ID NO: 8, and (c) interleukin-1β amino acid 231–235 of SEQ ID NO: 3.

3. An FGF-2 analogue of claim 2 wherein the amino acids corresponding to FGF-2 amino acids 118–122 of SEQ ID NO: 1 have been replaced with FGF-1 amino acids 115–121 of SEQ ID NO: 2.

4. An FGF-2 analogue of claim 2 wherein the amino acids corresponding to FGF-2 amino acids 118–122 of SEQ ID NO: 1 have been replaced with FGF-7 amino acids 154–162 of SEQ ID NO: 8.

5. An FGF-2 analogue of claim 2 wherein the amino acids corresponding to FGF-2 amino acids 118–122 of SEQ ID NO: 1 have boon replaced with interleukin-1β amino acids 231–235 of SEQ ID NO: 3.

6. An FGF-2 analogue wherein the amino acids corresponding to FGF-2 amino acids 115 to 124 of SEQ ID NO: 1 have been replaced with an amino acid sequence selected from the group consisting of (a) FGF-1 amino acids 112–125 of SEQ ID NO: 2, (b) FGF-3 amino acids 129–154 of SEQ ID NO: 4, (c) FGF-4 amino acids 169–178 of SEQ ID NO: 5, (d) FGF-5 amino acids 173–188 of SEQ ID NO: 6, (e) FGF-6 amino acids 171–180 of SEQ ID NO: 7, (f) FGF-7 amino acids 151–164 of SEQ ID NO: 8, (g) FGF-8 amino acids 136–156 of SEQ ID NO: 9, (h) FGF-9 amino acids 143–169 of SEQ ID NO: 10, and (i) interleukin-1β amino acids 231–235 of SEQ ID NO: 3 wherein said analogue is capable of binding to heparin.

7. An analogue according to claim 6 wherein the amino acids corresponding to amino acids 115 to 124 of SEQ ID NO: 1 have been replaced by FGF-1 amino acids 112–125 of SEQ ID NO: 2.

8. An analogue according to claim 6 wherein the amino acids corresponding to amino acids 115 to 124 of SEQ ID NO: 1 have been replaced by FGF-7 amino acids 151–164 of SEQ ID NO: 8.

9. An analogue according to claim 6 wherein the amino acids corresponding to amino acids 115 to 124 of SEQ ID NO: 1 have been replaced by interleukin-1β amino acids 231–235 of SEQ ID NO: 3.

* * * * *

UNITED STATES PATENT AND TRADEMARK OFFICE

CERTIFICATE OF CORRECTION

PATENT NO. : 5,491,220

DATED : February 13, 1996

INVENTOR(S) : Andrew P. Seddon, Lu-Yuan Li

It is certified that error appears in the above-identified patent and that said Letters Patent is hereby corrected as shown below:

| | |
|---|---|
| Col. 2, line 45 | Change "heparan" to -heparin-- |
| Col. 4, line 14 | Change "anglogenesis" to --angiogenesis-- |
| Col. 4, line 27 | Delete space between "Lys" and "120" to read --Lys120-- |
| Col. 4, line 29 | Delete space between "Thr" and "121" to read -- Thr121--. |
| Col. 7, line 54 | Delete space between "Ala" and "118" to read --Ala118-- |
| Col. 8, line 18 | Delete space between "Ala" and "118" to read --Ala118--. |
| Col. 11, line 60 | Change "adore" to --above-- |
| Col. 12, line 3 | Before "binding", insert --for-- |
| Col. 12, line 12 | Change "anglogenesis" to --angiogenesis-- |
| Col. 12, line 59 | Change "placed" to --replaced-- |
| Col. 12, line 60 | Change "no" to --not-- |
| Col. 12, line 65 | After "change", insert --in-- |
| Col. 19, line 26 | Change "heparan" to --heparin-- |

UNITED STATES PATENT AND TRADEMARK OFFICE
CERTIFICATE OF CORRECTION

PATENT NO. : 5,491,220
DATED : February 13,1996
INVENTOR(S) : Andrew P. Seddon, Lu-Yuan Li It is certified that error appears in the above-identified patent and that said Letters Patent is hereby corrected as shown below:

Col. 23, SEQ ID NO:3(ix)(A) In "NAME/KEY:", change "interleukin-1a" to --interleukin-1β--
Col. 33, SEQ ID NO:15(ix)(D) In "OTHER INFORMATION:" change "interleukin-1a" to --interleukin-1β--
Col 37, line 16 In claim 1(j), change "interleukin-113", to --interleukin 1β--
Col. 38, line 3 In Claim 5, change "boon" to --been--

Signed and Sealed this

Twenty-fifth Day of May, 1999

*Attest:*

Q. TODD DICKINSON

*Attesting Officer*

*Acting Commissioner of Patents and Trademarks*